(12) United States Patent
Raines et al.

(10) Patent No.: US 12,162,924 B2
(45) Date of Patent: Dec. 10, 2024

(54) METHOD FOR THE DESIGN OF FIBRILLAR COLLAGEN-MIMETIC PEPTIDE SELF-ASSEMBLIES

(71) Applicant: WISCONSIN ALUMNI RESEARCH FOUNDATION, Madison, WI (US)

(72) Inventors: Ronald T. Raines, Madison, WI (US); Ismet Tanrikulu, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 114 days.

(21) Appl. No.: 17/554,650

(22) Filed: Dec. 17, 2021

(65) Prior Publication Data

US 2022/0112269 A1   Apr. 14, 2022

Related U.S. Application Data

(62) Division of application No. 15/622,966, filed on Jun. 14, 2017, now Pat. No. 11,236,148.

(60) Provisional application No. 62/350,035, filed on Jun. 14, 2016.

(51) Int. Cl.
  *C07K 14/00* (2006.01)
  *C07K 14/78* (2006.01)

(52) U.S. Cl.
  CPC .................................. *C07K 14/78* (2013.01)

(58) Field of Classification Search
  CPC .................................................... C07K 14/78
  See application file for complete search history.

(56) References Cited

U.S. PATENT DOCUMENTS 9,725,499 B2 * 8/2017 Conticello ............. C07K 14/78

OTHER PUBLICATIONS

Andreasen Tet al. he Importance of Being Capped: Terminal Capping of an Amyloidogenic Peptide Affects Fibrillation Propensity and Fibril Morphology, Biochemistry 2014, 53:6968-6980).*
Keshwani (The Role of Cross-Chain Ionic Interactions for the Stability of Collagen Model Peptides, Biophysical Journal 2013, 105: 1681-1688).*
Bai, H.Y., et al., Fabrication of Au nanowires of uniform length and diameter using a monodisperse and rigid biomolecular template: Collagen-like triple helix. Angew. Chem. Int. Ed. 46, 3319-3322 (2007).
Banwell, E.F. et al., Rational design and application of responsive alpha-helical peptide hydrogels. Nat. Mat. 8, 596-600 (2009).
Brinckmann J., Collagens at a glance. Top. Curr. Chem. 247, 1-6 (2005).
Cejas, M.A. et al., Thrombogenic collagen-mimetic peptides: Self-assembly of triple helix-based fibrils driven by hydrophobic interactions. Proc. Natl. Acad. Sci. USA 105, 8513-8518 (2008).
Chattopadhyay, S. & Raines, R.T., Collagen-based biomaterials for wound healing. Biopolymers 101, 821-833 (2014).
Chen, Y.-S., et al., Thermodynamic and kinetic consequences of substituting glycine at different positions in a Pro-Hyp-Gly repeat collagen model peptide. Biopolymers 96, 60-68 (2011).
Cohen, S.N., et al., Construction of biologically functional bacterial plasmids in-vitro. Proc. Natl. Acad. Sci. USA 70, 3240-3244 (1973).
Fallas, J.A., et al., Solution structure of an ABC collagen heterotrimer reveals a single-register helix stabilized by electrostatic interactions. J. Biol. Chem. 284, 26851-26859 (2009).
Fields, G.B., Synthesis and biological applications of collagen-model triple-helical peptides. Org. Biomol. Chem. 8, 1237-1258 (2010).
Gauba, V. & Hartgerink, J.D., Surprisingly high stability of collagen ABC heterotrimer: Evaluation of side chain charge pairs. J. Am. Chem. Soc. 129, 15034-15041 (2007).
Gelman, R.A., et al., Collagen fibril formation: Evidence for a multistep process. J. Biol. Chem. 254, 180-186 (1979).
Gibson, D.G. et al., Enzymatic assembly of DNA molecules up to several hundred kilobases. Nat. Methods 6, 343-345 (2009).
Gottlieb, D., et al., Self-assembled collagen-like peptide fibers as templates for metallic nanowires. J. Mat. Chem. 18, 3865-3870 (2008).
Jiang, T., et al., Structurally homogeneous nanosheets from self-assembly of a collagen-mimetic peptide. Angew. Chem. Int. Ed. 53, 8367-8371 (2014).
Kaur, P. et al., Three-dimensional directed self-assembly of peptide nanowires into micrometer-sized crystalline cubes with nanoparticle joints. Angew. Chem. Int. Ed. 49, 8375-8378 (2010).
Khalil, A.S. & Collins, J.J., Synthetic biology: Applications come of age. Nat. Rev. Genet. 11, 367-379 (2010).
Kotch, F.W. & Raines, R.T., Self-assembly of synthetic collagen triple helices. Proc. Natl. Acad. Sci. USA 103, 3028-3033 (2006).
McGuinness, K., et al., Morphological diversity and polymorphism of self-assembling collagen peptides controlled by length of hydrophobic domains. ACS Nano 8, 12514-12523 (2014).
Meyers, M.A., et al., Biological materials: Structure and mechanical properties. Prog. Mat. Sci. 53, 1-206 (2008).
O'Leary, L.E.R., et al., Multi-hierarchical self-assembly of a collagen mimetic peptide from triple helix to nanofibre and hydrogel. Nat. Chem. 3, 821-828 (2011).
Persikov, A.V., et al., Electrostatic interactions involving lysine make major contributions to collagen triple-helix stability. Biochemistry 44, 1414-1422 (2005).
Persikov, A.V., et al., Prediction of collagen stability from amino acid sequence. J. Biol. Chem. 280, 19343-19349 (2005).
Persikov, A.V., et al., Amino acid propensities for the collagen triple-helix. Biochemistry 39, 14960-14967 (2000).
Rele, S. et al., D-Periodic collagen-mimetic microfibers. J. Am. Chem. Soc. 129, 14780-14787 (2007).
Richard-Blum, S., The collagen family. Cold Spring Harb. Perspect. Biol. 3, a004978 (2011).
Sarkar, B., et al., Self-assembly of fiber-forming collagen mimetic peptides controlled by triple-helical nucleation. J. Am. Chem. Soc. 136, 14417-14424 (2014).

(Continued)

*Primary Examiner* — Jeanette M Lieb
(74) *Attorney, Agent, or Firm* — Quarles & Brady, LLP

(57) ABSTRACT

Novel synthetic human scale collagen triple helices assemblies are disclosed. Methods of making self-assembling collagen mimetic peptides that self-assemble into human scale collagen are also disclosed.

25 Claims, 20 Drawing Sheets
(15 of 20 Drawing Sheet(s) Filed in Color)
Specification includes a Sequence Listing.

(56) References Cited

OTHER PUBLICATIONS

Seeman, N.C., Nanomaterials based on DNA. Annu. Rev. Biochem. 79, 65-87 (2010).
Siebler, C., et al., From azidoproline to functionalizable collagen. Chimia 67, 891-895 (2013).
Shoulders, M.D. & Raines, R.T., Collagen structure and stability. Annu. Rev. Biochem. 78, 929-958 (2009).
Smulders, M.M.J. et al., How to distinguish isodesmic from cooperative supramolecular polymerisation. Chem.—Eur. J. 16, 362-367 (2010).
Tanrikulu, I.C. & Raines, R.T., Optimal interstrand bridges for collagen-like biomaterials. J. Am. Chem. Soc. 136, 13490-13493 (2014).
Wess, T.J., Collagen fibril form and function. Adv. Protein Chem. 70, 341-374 (2005).
Xu, F. et al., Compositional control of higher order assembly using synthetic collagen peptides. J. Am. Chem. Soc. 134, 47-50 (2012).
Yamazaki, C.M. et al., A collagen-mimetic triple helical supramolecule that evokes integrin-dependent cell responses. Biomaterials 31, 1925-1934 (2010).
Zimenkov, Y. et al., Rational design of a reversible pH-responsive switch for peptide self-assembly. J. Am. Chem. Soc. 128, 6770-6771 (2006).
Tanrikulu, Peptide Tessellation yields micrometre-scale collagen triple helices, Nature Chemistry 2016, vol. 8 (Year: 2016).
Andreasen (The Importance of Being Capped: Terminal Capping of an Amyoidogenic Peptide Affects Fibrillation Propensity and Fibril Morphology, Biochemistry 2014, 53:6968-6980) (Year: 2014).
Bosshard (Protein stabilization by salt bridgers: concepts, experimental approaches and clarification of some misunderstandings, Journal of Molecular Recognition 2004, 17:1-16) (Year: 2004).
Keshwani (The Role of Cross-Chain Ionic Interactions for the Stability of Collagen Model Peptides, Biophysical Journal 2013, 105:1681-1688) (Year: 2013).

* cited by examiner

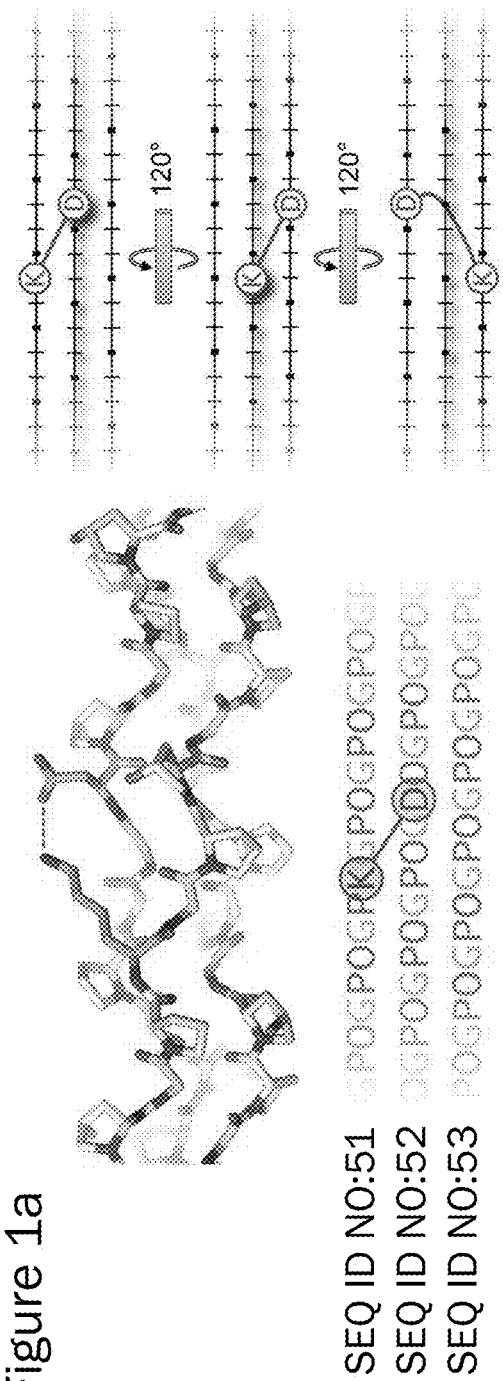
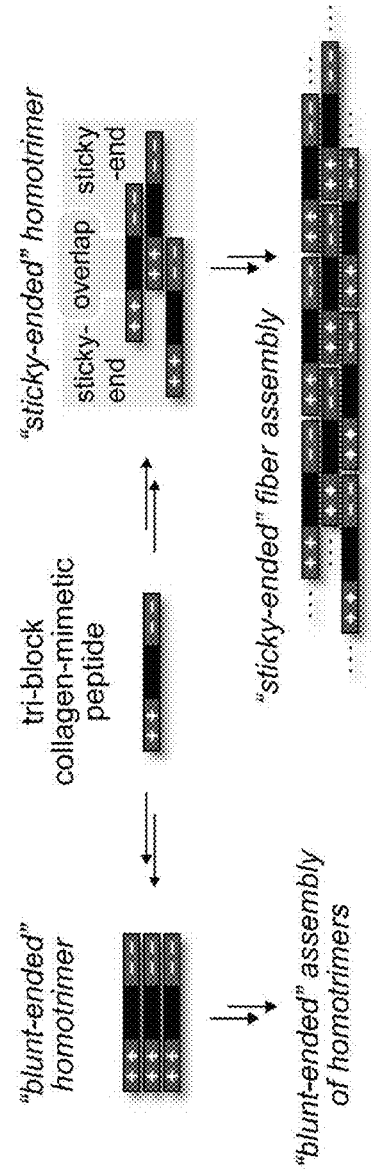
Figure 1a
SEQ ID NO:51
SEQ ID NO:52
SEQ ID NO:53
Figure 1b

Figure 2

POGPOGPOGPOGPOGPOG SEQ ID NO:54
POGPOGPOGPOGPOGPOG SEQ ID NO:55
POGPOGPOGPOGPOGPOG SEQ ID NO:53

(POG)₁₁ – 33mer    SEQ ID NO:10

(POG)₁₂ – 36mer    SEQ ID NO:11

(POG)₁₃ – 39mer    SEQ ID NO:12

Figure 7a
Figure 7b
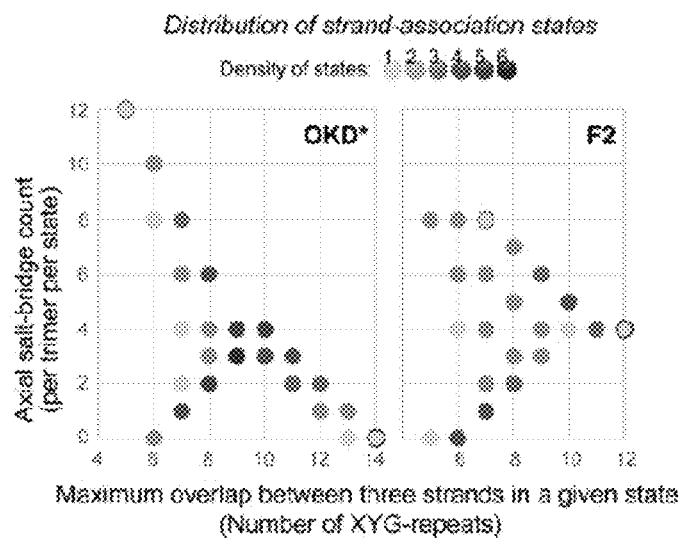
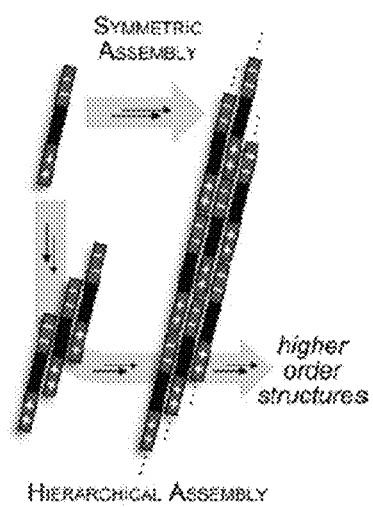
Figure 7c

OKD:

DOK:

KDO:

Figure 11a

| | |
|---|---|
| PO PK PK PK PK PO PO DO DO DO DO PO PO PO | SEQ ID NO:14 |
| PO PK PK PK PO PK PO DO DO DO PO DO PO PO | SEQ ID NO:15 |
| PO PK PK PO PO PK PO DK DO PO PO DO PO DO | SEQ ID NO:16 |

Figure 11b

| | |
|---|---|
| PK DO PK PO PO PO DO PK DO PK PO PO PO DO | SEQ ID NO:17 |
| PK DO PK PO PO PO DO ✦ PK DO PK PO PO PO DO | SEQ ID NO:18 |
| SEQ ID NO:18 | |

SEQUENCE LISTING

```
<160> NUMBER OF SEQ ID NOS: 58

<210> SEQ ID NO 1
<211> LENGTH: 36
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp

<400> SEQUENCE: 1

Pro Xaa Gly Pro Xaa Gly Pro Xaa Gly Pro Xaa Gly Pro Lys Gly Pro
1               5                   10                  15

Lys Gly Pro Lys Gly Pro Lys Gly Asp Xaa Gly Asp Xaa Gly Asp Xaa
            20                  25                  30

Gly Asp Xaa Gly
        35

<210> SEQ ID NO 2
<211> LENGTH: 42
<212> TYPE: PRT
<213> ORGANISM: Artificial Sequence
```

```
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 2

Pro Xaa Gly Pro Xaa Gly Pro Xaa Gly Pro Xaa Gly Pro Lys Gly Pro
1               5                   10                  15

Lys Gly Pro Lys Gly Pro Lys Gly Pro Xaa Gly Pro Xaa Gly Asp Xaa
            20                  25                  30

Gly Asp Xaa Gly Asp Xaa Gly Asp Xaa Gly
        35                  40

<210> SEQ ID NO 3
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
```

```
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp

<400> SEQUENCE: 3

Pro Xaa Gly Pro Xaa Gly Pro Lys Gly Pro Lys Gly Pro Lys Gly Pro
1               5                   10                  15

Lys Gly Pro Xaa Gly Asp Xaa Gly Asp Xaa Gly Asp Xaa Gly Asp Xaa
            20                  25                  30

Gly

<210> SEQ ID NO 4
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp

<400> SEQUENCE: 4

Pro Lys Gly Pro Lys Gly Pro Lys Gly Pro Lys Gly Asp Xaa Gly Asp
1               5                   10                  15

Xaa Gly Asp Xaa Gly Asp Xaa Gly
            20

<210> SEQ ID NO 5
<211> LENGTH: 48
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (26)..(26)
```

```
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp
<220> FEATURE:
<221> NAME/KEY: MOD_RES
<222> LOCATION: (44)..(44)
<223> OTHER INFORMATION: 4Hyp
<220> FEATURE:
<221> NAME/KEY: MOD_RES
<222> LOCATION: (47)..(47)
<223> OTHER INFORMATION: 4Hyp

<400> SEQUENCE: 5

Asp Xaa Gly Asp Xaa Gly Asp Xaa Gly Asp Xaa Gly Pro Lys Gly Pro
1               5                   10                  15

Lys Gly Pro Lys Gly Pro Lys Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa Gly
        35                  40                  45

<210> SEQ ID NO 6
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
```

-continued

```
<223> OTHER INFORMATION: 4Hyp
<220> FEATURE:
<221> NAME/KEY: MOD_RES
<222> LOCATION: (38)..(38)
<223> OTHER INFORMATION: 4Hyp

<400> SEQUENCE: 6

Asp Xaa Gly Asp Xaa Gly Asp Xaa Gly Asp Lys Gly Pro Lys Gly Pro
1               5                   10                  15

Lys Gly Pro Lys Gly Pro Xaa Gly Pro Xaa Gly Pro Xaa Gly Pro Xaa
            20                  25                  30

Gly Pro Xaa Gly Pro Xaa Gly
        35

<210> SEQ ID NO 7
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp

<400> SEQUENCE: 7

Asp Xaa Gly Asp Xaa Gly Asp Lys Gly Asp Lys Gly Pro Lys Gly Pro
1               5                   10                  15

Lys Gly Pro Xaa Gly Pro Xaa Gly Pro Xaa Gly Pro Xaa Gly
            20                  25                  30

<210> SEQ ID NO 8
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
```

```
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 8

Pro Xaa Gly Asp Xaa Gly Asp Xaa Gly Asp Xaa Gly Asp Xaa Gly Pro
1               5                   10                  15

Xaa Gly Pro Xaa Gly Pro Xaa Gly Pro Xaa Gly Pro Lys Gly Pro Lys
            20                  25                  30

Gly Pro Lys Gly Pro Lys Gly Pro Xaa Gly
            35                  40

<210> SEQ ID NO 9
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
```

```
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 9

Pro Lys Gly Pro Lys Gly Pro Lys Gly Pro Lys Gly Pro Xaa Gly Pro
1               5                   10                  15

Xaa Gly Asp Xaa Gly Asp Xaa Gly Asp Xaa Gly Asp Xaa Gly Pro Xaa
            20                  25                  30

Gly Pro Xaa Gly Pro Xaa Gly Pro Xaa Gly
        35                  40

<210> SEQ ID NO 10
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp

<400> SEQUENCE: 10

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly
```

```
<210> SEQ ID NO 11
<211> LENGTH: 36
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp

<400> SEQUENCE: 11

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly
        35

<210> SEQ ID NO 12
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
```

```
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp

<400> SEQUENCE: 12

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly
        35

<210> SEQ ID NO 13
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
```

```
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 13

Pro Xaa Gly Asp Xaa Gly Pro Xaa Gly Asp Xaa Gly Asp Xaa Gly Asp
1               5                   10                  15

Xaa Gly Pro Xaa Gly Pro Xaa Gly Pro Lys Gly Pro Lys Gly Pro Lys
                20                  25                  30

Gly Pro Xaa Gly Pro Lys Gly Pro Xaa Gly
            35                  40

<210> SEQ ID NO 14
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
```

```
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 14

Pro Xaa Gly Pro Lys Gly Pro Lys Gly Pro Lys Gly Pro Lys Gly Pro
1               5                   10                  15

Xaa Gly Pro Xaa Gly Asp Xaa Gly Asp Xaa Gly Asp Xaa Gly Asp Xaa
            20                  25                  30

Gly Pro Xaa Gly Pro Xaa Gly Pro Xaa Gly
        35                  40

<210> SEQ ID NO 15
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 15

Pro Xaa Gly Pro Lys Gly Pro Lys Gly Pro Lys Gly Pro Xaa Gly Pro
1               5                   10                  15

Lys Gly Pro Xaa Gly Asp Xaa Gly Asp Xaa Gly Asp Xaa Gly Pro Xaa
            20                  25                  30

Gly Asp Xaa Gly Pro Xaa Gly Pro Xaa Gly
        35                  40
```

```
<210> SEQ ID NO 16
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 16

Pro Xaa Gly Pro Lys Gly Pro Lys Gly Pro Xaa Gly Pro Xaa Gly Pro
1               5                   10                  15

Lys Gly Pro Xaa Gly Asp Lys Gly Asp Xaa Gly Pro Xaa Gly Pro Xaa
            20                  25                  30

Gly Asp Xaa Gly Pro Xaa Gly Asp Xaa Gly
        35                  40

<210> SEQ ID NO 17
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
```

```
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 17

Pro Lys Gly Asp Xaa Gly Pro Lys Gly Pro Xaa Gly Pro Xaa Gly Pro
1               5                   10                  15

Xaa Gly Asp Xaa Gly Pro Lys Gly Asp Xaa Gly Pro Lys Gly Pro Xaa
            20                  25                  30

Gly Pro Xaa Gly Pro Xaa Gly Asp Xaa Gly
        35                  40

<210> SEQ ID NO 18
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp

<400> SEQUENCE: 18

Pro Lys Gly Asp Xaa Gly Pro Lys Gly Pro Xaa Gly Pro Xaa Gly Pro
1               5                   10                  15

Xaa Gly Asp Xaa Gly
            20

<210> SEQ ID NO 19
<211> LENGTH: 32
<212> TYPE: PRT
<213> ORGANISM: Artificial Sequence
```

```
<220> FEATURE:
<223> OTHER INFORMATION: synthetic
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp

<400> SEQUENCE: 19

Pro Lys Gly Pro Lys Gly Pro Lys Gly Pro Xaa Gly Pro Xaa Gly Asp
1               5                   10                  15

Xaa Gly Asp Xaa Gly Asp Xaa Gly Pro Xaa Gly Pro Xaa Gly Pro Xaa
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: Ornithine
<220> FEATURE:
<221> NAME/KEY: MOD_RES
<222> LOCATION: (5)..(5)
<223> OTHER INFORMATION: Ornithine
<220> FEATURE:
<221> NAME/KEY: MOD_RES
<222> LOCATION: (8)..(8)
<223> OTHER INFORMATION: Ornithine
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
```

<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp

<400> SEQUENCE: 20

Pro Xaa Gly Pro Xaa Gly Pro Xaa Gly Pro Xaa Gly Pro Xaa Gly Asp
1               5                   10                  15

Xaa Gly Asp Xaa Gly Asp Xaa Gly Pro Xaa Gly Pro Xaa Gly Pro Xaa
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp

<400> SEQUENCE: 21

Pro Xaa Gly Pro Xaa Gly Pro Xaa Gly Pro Lys Gly Pro Lys Gly Pro
1               5                   10                  15

Lys Gly Pro Xaa Gly Pro Xaa Gly Asp Xaa Gly Asp Xaa Gly Asp Xaa
            20                  25                  30

<210> SEQ ID NO 22
<211> LENGTH: 33
<212> TYPE: PRT
<213> ORGANISM: Artificial Sequence
<220> FEATURE:
<223> OTHER INFORMATION: synthetic

```
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp

<400> SEQUENCE: 22

Pro Lys Gly Pro Lys Gly Pro Lys Gly Pro Xaa Gly Pro Xaa Gly Asp
1               5                   10                  15

Xaa Gly Asp Xaa Gly Asp Xaa Gly Pro Xaa Gly Pro Xaa Gly Pro Xaa
            20                  25                  30

Gly

<210> SEQ ID NO 23
<211> LENGTH: 41
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
```

```
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 23

Pro Xaa Gly Asp Xaa Gly Asp Xaa Gly Asp Xaa Gly Asp Xaa Gly Pro
1               5                   10                  15

Xaa Gly Pro Xaa Gly Pro Xaa Gly Pro Xaa Gly Pro Lys Gly Pro Lys
            20                  25                  30

Gly Pro Lys Gly Pro Lys Gly Pro Xaa
            35                  40

<210> SEQ ID NO 24
<211> LENGTH: 41
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 24

Pro Lys Gly Pro Lys Gly Pro Lys Gly Pro Lys Gly Pro Xaa Gly Pro
1               5                   10                  15

Xaa Gly Asp Xaa Gly Asp Xaa Gly Asp Xaa Gly Asp Xaa Gly Pro Xaa
            20                  25                  30
```

Gly Pro Xaa Gly Pro Xaa Gly Pro Xaa
            35                  40

<210> SEQ ID NO 25
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: Ornithine
<220> FEATURE:
<221> NAME/KEY: MOD_RES
<222> LOCATION: (14)..(14)
<223> OTHER INFORMATION: Ornithine
<220> FEATURE:
<221> NAME/KEY: MOD_RES
<222> LOCATION: (17)..(17)
<223> OTHER INFORMATION: Ornithine
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp

<400> SEQUENCE: 25

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Asp Xaa Gly Asp Xaa Gly Asp Xaa
            20                  25                  30

<210> SEQ ID NO 26
<211> LENGTH: 41
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:

```
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 26

Pro Xaa Gly Pro Xaa Gly Pro Xaa Gly Pro Xaa Gly Pro Lys Gly Pro
1               5                   10                  15

Lys Gly Pro Lys Gly Pro Lys Gly Pro Xaa Gly Pro Xaa Gly Asp Xaa
            20                  25                  30

Gly Asp Xaa Gly Asp Xaa Gly Asp Xaa
        35                  40

<210> SEQ ID NO 27
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
```

```
<221> NAME/KEY: MOD_RES
<222> LOCATION: (32)..(32)
<223> OTHER INFORMATION: 4Hyp

<400> SEQUENCE: 27

Pro Xaa Gly Pro Xaa Gly Pro Xaa Gly Pro Lys Gly Pro Lys Gly Pro
1               5                   10                  15

Lys Gly Pro Xaa Gly Pro Xaa Gly Asp Xaa Gly Asp Xaa Gly Asp Xaa
            20                  25                  30

Gly

<210> SEQ ID NO 28
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 28

Pro Xaa Gly Pro Xaa Gly Pro Xaa Gly Pro Lys Gly Pro Lys Gly Pro
1               5                   10                  15

Lys Gly Pro Lys Gly Pro Xaa Gly Pro Xaa Gly Asp Xaa Gly Asp Xaa
            20                  25                  30

Gly Asp Xaa Gly Asp Xaa Gly Pro Xaa Gly
        35                  40

<210> SEQ ID NO 29
<211> LENGTH: 24
<212> TYPE: PRT
<213> ORGANISM: Artificial Sequence
<220> FEATURE:
```

```
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (16)..(16)
<223> OTHER INFORMATION: Homocysteine
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp

<400> SEQUENCE: 29

Pro Xaa Gly Pro Xaa Gly Pro Xaa Gly Pro Xaa Gly Pro Xaa Gly Xaa
1               5                   10                  15

Xaa Gly Pro Xaa Gly Pro Xaa Gly
            20

<210> SEQ ID NO 30
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
```

-continued

```
<222> LOCATION: (23)..(23)
<223> OTHER INFORMATION: 4Hyp

<400> SEQUENCE: 30

Pro Xaa Gly Pro Xaa Gly Pro Cys Gly Pro Xaa Gly Pro Xaa Gly Pro
1               5                   10                  15

Xaa Gly Pro Xaa Gly Pro Xaa Gly
            20

<210> SEQ ID NO 31
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (22)..(22)
<223> OTHER INFORMATION: Homocysteine
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 31

Pro Xaa Gly Pro Xaa Gly Pro Xaa Gly Pro Lys Gly Pro Lys Gly Pro
1               5                   10                  15

Lys Gly Pro Lys Gly Xaa Xaa Gly Pro Xaa Gly Asp Xaa Gly Asp Xaa
            20                  25                  30

Gly Asp Xaa Gly Asp Xaa Gly Pro Xaa Gly
        35                  40

<210> SEQ ID NO 32
<211> LENGTH: 42
<212> TYPE: PRT
<213> ORGANISM: Artificial Sequence
```

```
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 32

Pro Xaa Gly Pro Xaa Gly Pro Cys Gly Pro Lys Gly Pro Lys Gly Pro
1               5                   10                  15

Lys Gly Pro Lys Gly Pro Xaa Gly Pro Xaa Gly Asp Xaa Gly Asp Xaa
            20                  25                  30

Gly Asp Xaa Gly Asp Xaa Gly Pro Xaa Gly
        35                  40

<210> SEQ ID NO 33
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (22)..(22)
<223> OTHER INFORMATION: Homocysteine
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
```

<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 33

Pro Xaa Gly Pro Xaa Gly Pro Xaa Gly Pro Lys Gly Pro Lys Gly Pro
1               5                   10                  15

Lys Gly Pro Lys Gly Xaa Xaa Gly Pro Xaa Gly Pro Xaa Gly Pro Xaa
            20                  25                  30

Gly Pro Xaa Gly Pro Xaa Gly Pro Xaa Gly
        35                  40

<210> SEQ ID NO 34
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES

```
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 34

Pro Xaa Gly Pro Xaa Gly Pro Cys Gly Pro Xaa Gly Pro Xaa Gly Pro
1               5                   10                  15

Xaa Gly Pro Xaa Gly Pro Xaa Gly Pro Xaa Gly Asp Xaa Gly Asp Xaa
            20                  25                  30

Gly Asp Xaa Gly Asp Xaa Gly Pro Xaa Gly
        35                  40

<210> SEQ ID NO 35
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 35

Pro Xaa Gly Pro Xaa Gly Pro Lys Gly Pro Lys Gly Pro Lys Gly Pro
1               5                   10                  15
```

```
Lys Gly Pro Xaa Gly Pro Xaa Gly Asp Xaa Gly Asp Xaa
            20                  25                  30

Gly Asp Xaa Gly Pro Xaa Gly Pro Xaa Gly
        35                  40
```

<210> SEQ ID NO 36
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 36

```
Pro Xaa Gly Pro Lys Gly Pro Lys Gly Pro Lys Gly Pro Lys Gly Pro
1               5                   10                  15

Xaa Gly Pro Xaa Gly Asp Xaa Gly Asp Xaa Gly Asp Xaa Gly Asp Xaa
            20                  25                  30

Gly Pro Xaa Gly Pro Xaa Gly Pro Xaa Gly
        35                  40
```

<210> SEQ ID NO 37
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)

```
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 37

Pro Xaa Gly Pro Xaa Gly Pro Xaa Gly Pro Lys Gly Pro Lys Gly Pro
1               5                   10                  15

Lys Gly Pro Xaa Gly Pro Lys Gly Pro Xaa Gly Asp Xaa Gly Asp Xaa
            20                  25                  30

Gly Asp Xaa Gly Pro Xaa Gly Asp Xaa Gly
        35                  40

<210> SEQ ID NO 38
<211> LENGTH: 41
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
```

```
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 38

Pro Xaa Gly Asp Xaa Gly Pro Xaa Gly Asp Xaa Gly Asp Xaa Gly Asp
1               5                   10                  15

Xaa Gly Pro Xaa Gly Pro Xaa Gly Pro Lys Gly Pro Lys Gly Pro Lys
            20                  25                  30

Gly Pro Xaa Gly Pro Lys Gly Pro Xaa
        35                  40

<210> SEQ ID NO 39
<211> LENGTH: 41
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: Ornithine
<220> FEATURE:
<221> NAME/KEY: MOD_RES
<222> LOCATION: (32)..(32)
<223> OTHER INFORMATION: Ornithine
<220> FEATURE:
<221> NAME/KEY: MOD_RES
<222> LOCATION: (35)..(35)
```

```
<223> OTHER INFORMATION: Ornithine
<220> FEATURE:
<221> NAME/KEY: MOD_RES
<222> LOCATION: (38)..(38)
<223> OTHER INFORMATION: Ornithine
<220> FEATURE:
<221> NAME/KEY: MOD_RES
<222> LOCATION: (41)..(41)
<223> OTHER INFORMATION: 4Hyp

<400> SEQUENCE: 39

Pro Xaa Gly Asp Xaa Gly Asp Xaa Gly Asp Xaa Gly Asp Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa
        35                  40

<210> SEQ ID NO 40
<211> LENGTH: 41
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: Ornithine
<220> FEATURE:
<221> NAME/KEY: MOD_RES
<222> LOCATION: (17)..(17)
<223> OTHER INFORMATION: Ornithine
<220> FEATURE:
<221> NAME/KEY: MOD_RES
<222> LOCATION: (20)..(20)
<223> OTHER INFORMATION: Ornithine
<220> FEATURE:
<221> NAME/KEY: MOD_RES
<222> LOCATION: (23)..(23)
<223> OTHER INFORMATION: Ornithine
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
```

```
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 40

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Asp Xaa
            20                  25                  30

Gly Asp Xaa Gly Asp Xaa Gly Asp Xaa
        35                  40

<210> SEQ ID NO 41
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: Ornithine
<220> FEATURE:
<221> NAME/KEY: MOD_RES
<222> LOCATION: (17)..(17)
<223> OTHER INFORMATION: Ornithine
<220> FEATURE:
<221> NAME/KEY: MOD_RES
<222> LOCATION: (20)..(20)
<223> OTHER INFORMATION: Ornithine
<220> FEATURE:
<221> NAME/KEY: MOD_RES
<222> LOCATION: (23)..(23)
<223> OTHER INFORMATION: Ornithine
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
```

<223> OTHER INFORMATION: 4Hyp

<400> SEQUENCE: 41

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Asp Xaa
            20                  25                  30

Gly Asp Xaa Gly Asp Xaa Gly Asp Xaa Gly
        35                  40

<210> SEQ ID NO 42
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 42

Pro Xaa Gly Pro Xaa Gly Pro Lys Gly Pro Lys Gly Pro Lys Gly Pro
1               5                   10                  15

Xaa Gly Pro Lys Gly Pro Xaa Gly Pro Xaa Gly Asp Xaa Gly Pro Xaa
            20                  25                  30

Gly Asp Xaa Gly Asp Xaa Gly Asp Xaa Gly
        35                  40

<210> SEQ ID NO 43
<211> LENGTH: 42
<212> TYPE: PRT
<213> ORGANISM: Artificial Sequence
<220> FEATURE:
<223> OTHER INFORMATION: synthetic -continued

```
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
<222> LOCATION: (35)..(35)
<223> OTHER INFORMATION: 4Hyp
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 43

Pro Xaa Gly Asp Xaa Gly Pro Xaa Gly Pro Lys Gly Pro Lys Gly Pro
1               5                   10                  15

Xaa Gly Pro Xaa Gly Pro Lys Gly Pro Xaa Gly Asp Lys Gly Asp Xaa
            20                  25                  30

Gly Pro Xaa Gly Pro Xaa Gly Asp Xaa Gly
        35                  40

<210> SEQ ID NO 44
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
```

<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid

<400> SEQUENCE: 44

Xaa Xaa Gly Xaa Xaa Gly Xaa Xaa Gly Xaa Xaa Gly Xaa Xaa Gly Xaa
1               5                   10                  15

Lys Gly Xaa Xaa Gly Xaa Xaa Gly Xaa Xaa Gly Xaa Xaa Gly Xaa Xaa
            20                  25                  30

Gly Xaa Xaa Gly Xaa Xaa Gly Xaa Xaa Gly
        35                  40

<210> SEQ ID NO 45
<211> LENGTH: 42
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

```
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid

<400> SEQUENCE: 45

Xaa Xaa Gly Xaa Xaa Gly Xaa Xaa Gly Xaa Xaa Gly Xaa Xaa Gly Xaa
1               5                   10                  15

Lys Gly Xaa Xaa Gly Xaa Xaa Gly Xaa Xaa Gly Xaa Xaa Gly Xaa Xaa
            20                  25                  30

Gly Asp Xaa Gly Xaa Xaa Gly Xaa Xaa Gly
        35                  40

<210> SEQ ID NO 46
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: MOD_RES
<222> LOCATION: (2)..(2)
<223> OTHER INFORMATION: 4Hyp
<220> FEATURE:
<221> NAME/KEY: MISC_FEATURE
<222> LOCATION: (4)..(5)
<223> OTHER INFORMATION: When (4) is Pro, (5) is Lys. When (4) is Asp,
      (5) is 4Hyp
<220> FEATURE:
<221> NAME/KEY: X
<222> LOCATION: (4)..(4)
<223> OTHER INFORMATION: X is Pro or Asp
<220> FEATURE:
<221> NAME/KEY: REPEAT
<222> LOCATION: (4)..(6)
<223> OTHER INFORMATION: the number of repeats of the string of residues
      4-6 is zero or any positive integer
<220> FEATURE:
<221> NAME/KEY: X
<222> LOCATION: (5)..(5)
<223> OTHER INFORMATION: X is Lys or 4Hyp
<220> FEATURE:
```

```
<221> NAME/KEY: MISC_FEATURE
<222> LOCATION: (7)..(8)
<223> OTHER INFORMATION: When (7) is Pro, (8) is 4Hyp. When (7) is Asp,
      (8) is Lys
<220> FEATURE:
<221> NAME/KEY: X
<222> LOCATION: (7)..(7)
<223> OTHER INFORMATION: X is Pro or Asp
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: X
<222> LOCATION: (8)..(8)
<223> OTHER INFORMATION: X is Lys or 4Hyp
<220> FEATURE:
<221> NAME/KEY: MISC_FEATURE
<222> LOCATION: (10)..(11)
<223> OTHER INFORMATION: When (10) is Pro, (11) is Lys. When (10) is
      Asp, (11) is 4Hyp.
<220> FEATURE:
<221> NAME/KEY: X
<222> LOCATION: (10)..(10)
<223> OTHER INFORMATION: X is Pro or Asp
<220> FEATURE:
<221> NAME/KEY: REPEAT
<222> LOCATION: (10)..(12)
<223> OTHER INFORMATION: the number of repeats of the string of residues
      10-12 is zero or any positive integer
<220> FEATURE:
<221> NAME/KEY: X
<222> LOCATION: (11)..(11)
<223> OTHER INFORMATION: X is Lys or 4Hyp
<220> FEATURE:
<221> NAME/KEY: REPEAT
<222> LOCATION: (13)..(15)
<223> OTHER INFORMATION: the number of repeats of the string of residues
      13-15 is zero or any positive integer
<220> FEATURE:
<221> NAME/KEY: MOD_RES
<222> LOCATION: (14)..(14)
<223> OTHER INFORMATION: 4Hyp

<400> SEQUENCE: 46

Pro Xaa Gly Xaa Xaa Gly Xaa Xaa Gly Xaa Xaa Gly Pro Xaa Gly
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: MOD_RES
<222> LOCATION: (2)..(2)
<223> OTHER INFORMATION: 4Hyp
<220> FEATURE:
<221> NAME/KEY: REPEAT
<222> LOCATION: (4)..(6)
<223> OTHER INFORMATION: the number of repeats of the string of residues
      4-6 is zero or any positive integer
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: MOD_RES
<222> LOCATION: (8)..(8)
```

```
<223> OTHER INFORMATION: 4Hyp
<220> FEATURE:
<221> NAME/KEY: REPEAT
<222> LOCATION: (10)..(12)
<223> OTHER INFORMATION: the number of repeats of the string of residues
      10-12 is zero or any positive integer
<220> FEATURE:
<221> NAME/KEY: MOD_RES
<222> LOCATION: (11)..(11)
<223> OTHER INFORMATION: 4Hyp
<220> FEATURE:
<221> NAME/KEY: REPEAT
<222> LOCATION: (13)..(15)
<223> OTHER INFORMATION: the number of repeats of the string of residues
      13-15 is zero or any positive integer
<220> FEATURE:
<221> NAME/KEY: MOD_RES
<222> LOCATION: (14)..(14)
<223> OTHER INFORMATION: 4Hyp

<400> SEQUENCE: 47

Pro Xaa Gly Pro Lys Gly Pro Xaa Gly Asp Xaa Gly Pro Xaa Gly
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: MOD_RES
<222> LOCATION: (2)..(2)
<223> OTHER INFORMATION: 4Hyp
<220> FEATURE:
<221> NAME/KEY: REPEAT
<222> LOCATION: (4)..(6)
<223> OTHER INFORMATION: the number of repeats of the string of residues
      4-6 is zero or any positive integer
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: REPEAT
<222> LOCATION: (10)..(12)
<223> OTHER INFORMATION: the number of repeats of the string of residues
      10-12 is zero or any positive integer
<220> FEATURE:
<221> NAME/KEY: MOD_RES
<222> LOCATION: (11)..(11)
<223> OTHER INFORMATION: 4Hyp
<220> FEATURE:
<221> NAME/KEY: REPEAT
<222> LOCATION: (13)..(15)
<223> OTHER INFORMATION: the number of repeats of the string of residues
      13-15 is zero or any positive integer
<220> FEATURE:
<221> NAME/KEY: MOD_RES
<222> LOCATION: (14)..(14)
<223> OTHER INFORMATION: 4Hyp

<400> SEQUENCE: 48

Pro Xaa Gly Pro Lys Gly Asp Lys Gly Asp Xaa Gly Pro Xaa Gly
1               5                   10                  15

<210> SEQ ID NO 49
<211> LENGTH: 15
<212> TYPE: PRT
```

```
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: MOD_RES
<222> LOCATION: (2)..(2)
<223> OTHER INFORMATION: 4Hyp
<220> FEATURE:
<221> NAME/KEY: REPEAT
<222> LOCATION: (4)..(6)
<223> OTHER INFORMATION: the number of repeats of the string of residues
      4-6 is zero or any positive integer
<220> FEATURE:
<221> NAME/KEY: MOD_RES
<222> LOCATION: (5)..(5)
<223> OTHER INFORMATION: 4Hyp
<220> FEATURE:
<221> NAME/KEY: REPEAT
<222> LOCATION: (7)..(9)
<223> OTHER INFORMATION: the number of repeats of the string of residues
      7-9 is zero or any positive integer
<220> FEATURE:
<221> NAME/KEY: MOD_RES
<222> LOCATION: (8)..(8)
<223> OTHER INFORMATION: 4Hyp
<220> FEATURE:
<221> NAME/KEY: REPEAT
<222> LOCATION: (10)..(12)
<223> OTHER INFORMATION: the number of repeats of the string of residues
      10-12 is zero or any positive integer
<220> FEATURE:
<221> NAME/KEY: REPEAT
<222> LOCATION: (13)..(15)
<223> OTHER INFORMATION: the number of repeats of the string of residues
      13-15 is zero or any positive integer
<220> FEATURE:
<221> NAME/KEY: MOD_RES
<222> LOCATION: (14)..(14)
<223> OTHER INFORMATION: 4Hyp

<400> SEQUENCE: 49

Pro Xaa Gly Asp Xaa Gly Pro Xaa Gly Pro Lys Gly Pro Xaa Gly
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(3)
<223> OTHER INFORMATION: the number of repeats of the string of residues
      1-3 is zero or any positive integer
<220> FEATURE:
<221> NAME/KEY: MOD_RES
<222> LOCATION: (2)..(2)
<223> OTHER INFORMATION: 4Hyp
<220> FEATURE:
<221> NAME/KEY: REPEAT
<222> LOCATION: (4)..(6)
<223> OTHER INFORMATION: the number of repeats of the string of residues
      4-6 is zero or any positive integer
<220> FEATURE:
<221> NAME/KEY: MOD_RES
<222> LOCATION: (5)..(5)
<223> OTHER INFORMATION: 4Hyp
<220> FEATURE:
<221> NAME/KEY: REPEAT
<222> LOCATION: (7)..(9)
<223> OTHER INFORMATION: the number of repeats of the string of residues
```

```
      7-9 is zero or any positive integer
<220> FEATURE:
<221> NAME/KEY: REPEAT
<222> LOCATION: (10)..(12)
<223> OTHER INFORMATION: the number of repeats of the string of residues
      10-12 is zero or any positive integer
<220> FEATURE:
<221> NAME/KEY: REPEAT
<222> LOCATION: (13)..(15)
<223> OTHER INFORMATION: the number of repeats of the string of residues
      13-15 is zero or any positive integer
<220> FEATURE:
<221> NAME/KEY: MOD_RES
<222> LOCATION: (14)..(14)
<223> OTHER INFORMATION: 4Hyp

<400> SEQUENCE: 50

Pro Xaa Gly Asp Xaa Gly Asp Lys Gly Pro Lys Gly Pro Xaa Gly
1               5                   10                  15

<210> SEQ ID NO 51
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp

<400> SEQUENCE: 51

Pro Xaa Gly Pro Xaa Gly Pro Lys Gly Pro Xaa Gly Pro Xaa Gly Pro
1               5                   10                  15

Xaa Gly

<210> SEQ ID NO 52
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp
```

```
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp

<400> SEQUENCE: 52

Gly Pro Xaa Gly Pro Xaa Gly Pro Xaa Gly Asp Xaa Gly Pro Xaa Gly
1               5                   10                  15

Pro Xaa

<210> SEQ ID NO 53
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (10)..(10)
<223> OTHER INFORMATION: 4Hyp
<220> FEATURE:
<221> NAME/KEY: MOD_RES
<222> LOCATION: (13)..(13)
<223> OTHER INFORMATION: 4Hyp
<220> FEATURE:
<221> NAME/KEY: MOD_RES
<222> LOCATION: (16)..(16)
<223> OTHER INFORMATION: 4Hyp

<400> SEQUENCE: 53

Xaa Gly Pro Xaa Gly Pro Xaa Gly Pro Xaa Gly Pro Xaa Gly Pro Xaa
1               5                   10                  15

Gly Pro

<210> SEQ ID NO 54
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
```

```
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp

<400> SEQUENCE: 54

Pro Xaa Gly Pro Xaa Gly Pro Xaa Gly Pro Xaa Gly Pro Xaa Gly Pro
1               5                   10                  15

Xaa Gly

<210> SEQ ID NO 55
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp

<400> SEQUENCE: 55

Gly Pro Xaa Gly Pro Xaa Gly Pro Xaa Gly Pro Xaa Gly Pro Xaa Gly
1               5                   10                  15

Pro Xaa

<210> SEQ ID NO 56
<211> LENGTH: 36
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
```

```
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid

<400> SEQUENCE: 56

Xaa Xaa Gly Xaa Xaa Gly Xaa Xaa Gly Xaa Xaa Gly Xaa Xaa Gly Xaa
1               5                   10                  15

Xaa Gly Xaa Xaa Gly Xaa Xaa Gly Xaa Xaa Gly Xaa Xaa Gly Xaa Xaa
            20                  25                  30

Gly Xaa Xaa Gly
        35

<210> SEQ ID NO 57
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
```

```
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid

<400> SEQUENCE: 57

Xaa Xaa Gly Xaa Xaa Gly Xaa Xaa Gly Xaa Xaa Gly Xaa Xaa Gly Xaa
1               5                   10                  15

Xaa Gly Xaa Xaa Gly Xaa Xaa Gly Xaa Xaa Gly Xaa Xaa Gly Xaa Xaa
            20                  25                  30

Gly

<210> SEQ ID NO 58
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(35)
```

-continued

```
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid

<400> SEQUENCE: 58

Xaa Xaa Gly Xaa Xaa Gly Xaa Xaa Gly Xaa Xaa Gly Xaa Xaa Gly Xaa
1               5                   10                  15

Xaa Gly Xaa Xaa Gly Xaa Xaa Gly Xaa Xaa Gly Xaa Xaa Gly Xaa Xaa
            20                  25                  30

Gly Xaa Xaa Gly Xaa Xaa Gly
        35
```

METHOD FOR THE DESIGN OF FIBRILLAR COLLAGEN-MIMETIC PEPTIDE SELF-ASSEMBLIES

CROSS-REFERENCE TO RELATED APPLICATIONS

This application is a divisional application claiming priority to U.S. application Ser. No. 15/622,966, filed on Jun. 14, 2017, which claims priority to U.S. Provisional Application 62/350,035 filed Jun. 14, 2016, the content of which is incorporated by reference in its entirety.

STATEMENT REGARDING FEDERALLY SPONSORED RESEARCH OR DEVELOPMENT

This invention was made with government support under AR044276 awarded by the National Institutes of Health. The government has certain rights in the invention.

SEQUENCE LISTING STATEMENT

A Sequence Listing accompanies this application and is submitted as an ASCII text file of the sequence listing named "960296_04263_ST25.txt" which is 60,967 bytes in size and was created on Dec. 17, 2021. The sequence listing is electronically submitted via EFS-Web with the application and is incorporated herein by reference in its entirety.

BACKGROUND

Strict base-pairing rules enable the DNA double helix to store, recall, and replicate biochemical information. The ability of DNA strands to anneal in a sequence-specific manner also allows DNA to form duplexes with single-stranded overhangs. These "sticky ends" enable duplexes with complementary overhangs to anneal and thereby extend the double helix. The ensuing cohesive assemblies can far exceed the size of constituent strands and underlie the fields of molecular biology[1,2], synthetic biology[3], and DNA nanotechnology[4]. Likewise, the sticky-ended self-assembly of certain α-helical peptides can yield long, though thick, bundles[5,6].

Similar to that of DNA and α-helical bundles, the structure of collagen features intercoiled strands. Collagen is the predominant structural protein in animals[7,8]. Accordingly, non-human collagen is the most common biomaterial in the clinic, but its use can be complicated by allergic reaction and pathogen transmission[9]. Natural collagen contains a high level of post-translational modification and its biosynthesis is regulated tightly[10], complicating the heterologous production of human collagen, which has strands of ~10³ residues (~300 nm in length). Conversely, chemical synthesis can offer only collagen-mimetic peptides (CMPs) of ~30 residues (~10 nm), which have little practical utility[11]. Endowing CMPs with utility requires their assembly into "human-scale" collagen.

The assembly of both DNA strands into double helices and α-helical peptides into coiled-coils relies on side-chain-side-chain interactions. In contrast, triple-helical association of collagen proceeds through main-chain-main-chain interactions, influenced only weakly by primary sequence. The structure of the collagen triple helix is defined by the repeating Xaa-Yaa-Gly tripeptide units (XaaYaaGly-repeats) of its strands, in which proline (Pro; P) and 4-hydroxyproline (Hyp; O) are abundant in the Xaa and Yaa positions, respectively, and a glycine residue (Gly; G) is essential in every third position[12]. The resulting sequence favors the formation of left-handed polyproline-type II helices, which associate into right-handed triple helices through main-chain-main-chain hydrogen bonds. A tight, compact association is attained by a single-residue shift that places one Xaa, Yaa, and Gly residue from each strand at every helical cross-section, creating three distinct strand "registers" (FIG. 1a). The resulting scaffold directs all side chains away from the central triple-helical axis. The radiating side-chains allow for extensive functionalization[13], but limit options for CMP assembly. Moreover, a "blunt-ended" association state is accessible to all CMPs, regardless of sequence.

Due to the secondary role of sequence in collagen structure, the design of a CMP that avoids blunt-ended trimers has been a challenge. During the past decade, our group and others have reported on strategies that enable CMPs to form extended structures[14-21]. Each of these systems, however, relies on the tedious crosslinking of three strands to enforce sticky ends or yields thick fibers of limited utility.

Accordingly, there is a need in the art for compositions and methods for creating self-assembling human-scale collagen.

SUMMARY OF THE INVENTION

Other objects, advantages, and features of the present invention will become apparent upon review of the specification, drawings, and claims.

In one aspect, the disclosure provides a method for designing a collagen mimetic peptide capable of self-assembly comprising: (a) preparing a plurality of self-assembling collagen mimetic peptides comprising Xaa-Yaa-Gly tripeptide repeats, wherein the number of tripeptide repeats ($n_T$) is $3v\pm1$, wherein v is a positive integer, wherein the peptide is n residues in length, wherein $n=n_T \times 3$; and (b) allowing at least two of the collagen mimetic peptides to self-assemble.

In another aspect, the disclosure provides a symmetrical triple helical collagen protein comprising: a plurality of self-assembling collagen mimetic peptides comprising Xaa-Yaa-Gly tripeptide repeats, wherein the number of tripeptide repeats ($n_T$) is $3v\pm1$, wherein v is a positive integer, wherein the peptide is n residues in length, wherein $n=n_T \times 3$; wherein the collagen mimetic peptides self-assemble to form the symmetrical triple helical collagen protein.

In a further aspect, the disclosure provides a synthetic symmetrical triple helical collagen assembly comprising collagen mimetic peptides comprising:

$$(POG)_n(PKG/DOG)_m(POG/DKG)_p(DOG/PKG)_q(POG)_r \quad (SEQ\ ID\ NO:\ 46)$$

wherein "/" signifies one or the other tripeptide, but not both (for example $(PKD/DOC)_m$ signifies $(PKD)_m$ or $(DOG)_m$), and wherein n, m, p, q and r are selected from 0 or are independently selected from a positive integer, e.g. 1-10 and wherein $n_T=n+m+p+q+r=3v\pm1>0$. In some aspects, $n_T$ is >3 or wherein $n_T>6$. In some aspects, m=q.

In some aspects, the collagen assembly comprises peptides selected from one of the following sequences:

$$(POG)_n(PKG)_m(POG)_p(DOG)_q(POG)_r; \quad (SEQ\ ID\ NO:\ 47)$$

-continued (POG)$_n$(PKG)$_m$(DKG)$_p$(DOG)$_q$(POG)$_r$;  (SEQ ID NO: 48)

(POG)$_n$(DOG)$_m$(POG)$_p$(PKG)$_q$(POG)$_r$;  (SEQ ID NO: 49)
or (POG)$_n$(DOG)$_m$(DKG)$_p$(PKG)$_q$(POG)$_r$,  (SEQ ID NO: 50)

wherein n, m, p, q, and r are selected from 0 or a positive integer, e.g. 1-10 and wherein $n_T$=n+m+p+q+r=3v±1>0. In some aspects, m=q. In some aspects, only one of n, p, or r are 0.

DESCRIPTION OF THE DRAWINGS

This patent application file contains at least one drawing executed in color. Copies of this patent or patent application publication with color drawing(s) will be provided by the Office upon request and payment of the necessary fee.

FIG. 1a depicts the molecular structure of the collagen triple helix and depictions of an axial salt bridge. The model, built based on the PDB entry 3u29 on PyMOL v1.3, presents an interstrand Lys (cyan) • • • Asp (red) salt bridge over a [(POG)$_n$]$_3$ background with Gly residues shown in yellow. In the triple helix, salt-bridging residues are indicated by interconnected blue and red circles. Pro/Hyp and Gly residues on a CMP are depicted simply as bars and dots on a line to emphasize the Lys • • • Asp salt bridges.

FIG. 1b depicts fibrillar self-assembly of tri-block CMPs through blunt-ended[15] and sticky-ended[19] pathways.

FIG. 2 depicts the effect of CMP size on symmetric assembly. Collagen structure requires a single-residue stagger between XaaYaaGly-units of all strands of a triple helix (top). This requirement prevents (XaaYaaGly)$_{12}$ (SEQ ID NO:56) strands from associating symmetrically, while such assemblies are accessible through (XaaYaaGly)$_{11}$ (SEQ ID NO:57) and (XaaYaaGly)$_{13}$ (SEQ ID NO:58) strands (bottom).

FIG. 7a depicts a comparison of strand-association states available to OKD and F2 peptides indicating states leading to blunt-ends (black outline) and to the dominant sticky-ended assemblies (red outline). *This distribution of states is shared with all 4sb-derived peptides.

FIG. 7b depicts the comparison of symmetric vs. hierarchical assembly.

FIG. 7c depicts the design of multi-component fibers through a symmetric-assembly template. Complex building-blocks (red and blue bars) generated on a strand-association pattern set by a symmetric assembly (empty bars) can similarly achieve symmetric assembly.

FIG. 11a depicts examples of symmetrically designed peptides that allow perfect charge-pairing. Among 73 sequences that allow symmetric assembly for 4sb-like systems ($n_T$=14; yx-class), all non-repetitive sequences produce unique perfectly-paired states.

FIG. 11b shows repeating sequences that support multiple symmetries and are the only exceptions. This example is composed of two repeats of a shorter ($n_T$=7; xy-class) "symmetric" peptide, which also satisfies $n_T$=14 symmetry. In this way, perfectly-paired assemblies can be accessed through two distinct symmetric association states. This example is one of 3 from a possible 73.

DETAILED DESCRIPTION

Figure 1C:
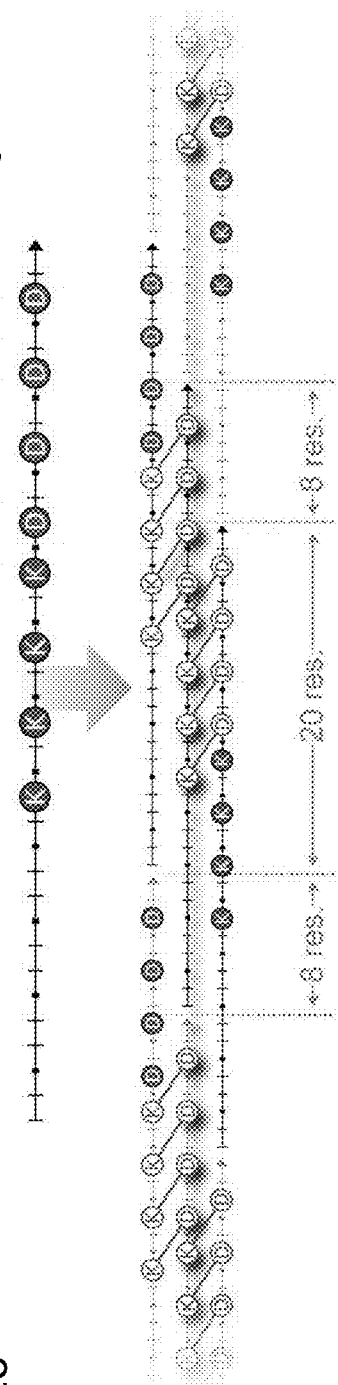
FIG. 1c depicts self-assembly of the F2 peptide[21]. Unpaired Lys and Asp residues implicated in unintended associations are indicated with filled circles.

Collagen is the most abundant protein in vertebrates, occurring in virtually every tissue, including, for example, skin, tendon, bone, blood vessel, cartilage, ligament, and teeth. Collagen serves as the fundamental structural protein for vertebrate tissues. Collagen abnormalities are associated with a wide variety of human diseases, including arthritis, rheumatism, brittle bones, atherosclerosis, cirrhosis, and eye cataracts. Collagen is also critically important in wound healing. Collagen's biological significance has made it a common target for biomaterials engineering, encouraging the development of self-assembling synthetic peptide systems that mimic the triple-helical architecture of collagen. Though collagen mimetic peptides have been previously produced, both the peptides and their self-assemblies have been shorter and not at the scale of human collagens. Furthermore, previously produced collagen assemblies did not use symmetry as in the present invention. Therefore, there is a need for novel synthetic "human-scale" triple helical proteins such as collagen.

This disclosure provides self-assembling collagen mimetic peptides that can assemble into symmetrical collagen assemblies that are human scale and methods of making them. The symmetrical collagen assembly comprises three strands of collagen that form a trimer (e.g. a first, second and third strand). "Strand" as used herein, refers to one of the three intertwined backbones that make up the triple helix. In the case of an assembly, each strand is made up of many peptides positioned end-to-end to form a continuous and structurally coherent polyproline type-II helix, which, when viewed from far away, resemble one continuous collagen strand in a large triple-helical assembly. Strands are only defined when multiple peptides associate through interstrand interactions. Use of this terminology does not imply the elongation of the peptides in the same register into a continuous peptide sequence, as peptide self-assembly always proceeds through interactions with peptides in neighboring registers. In some aspects, the first, second and third strand of the collagen are associated by interstrand interactions. In some embodiments, the interstrand interactions are interstrand salt bridges.

The present disclosure provides methods for producing symmetrical collagen assemblies which have not been previously described. Although various sticky-ended CMP assemblies have been produced up until this point, none of the methods of making these CMPs have used symmetrical design. CMP self-assemblies allow any group of symmetrically assembled peptide(s) (single or multimers) to assemble with any other group of symmetrically-assembled peptides (single or multimer). Each of these groups could be a single peptide or a multimer, e.g. dimer/trimer/10-mer/100-mer/ etc. As described herein, peptides that associate with each other with $n_T$-residue offsets (see FIG. 1e), allow multiple routes of assembling the symmetrical collagen assemblies. This type of assembly is not something other systems can do, unless they chemically link all three strands to preconstruct a trimer (e.g. Kotch, Raines 2006 *PNAS*). For example, you cannot take the F2 peptide in FIG. 1c, make into dimers and expect the dimers to further associate, while this can occur using the peptides of the present invention. For example, OKD (FIG. 1f) is a self-assembling peptide of the present invention. Disclosed herein is a method for making a collagen mimetic peptide capable of self-assembly comprising: (a) preparing a plurality of self-assembling collagen mimetic peptides comprising Xaa-Yaa-Gly tripeptide repeats, wherein the number of tripeptide repeats ($n_T$) is 3v±1, wherein v is a positive integer, wherein the peptide is n residues in length, wherein n=$n_T$×3; and (b) allowing at least two of the collagen mimetic peptides to self-assemble with an $n_T$-residue offset to form a collagen assembly.

Disclosed herein is a method for making a collagen mimetic peptide capable of self-assembly comprising: (a) preparing a plurality of self-assembling collagen mimetic peptides comprising Xaa-Yaa-Gly tripeptide repeats, wherein the number of tripeptide repeats ($n_T$) is 3v±1, wherein v is a positive integer and the wherein the last tripetide repeat of the peptide is missing a Gly, wherein the peptide is n residues in length, wherein n=3(3v±1)−1; and (b) allowing at least two of the collagen mimetic peptides to self-assemble with an $n_T$-residue offset to form a collagen assembly. Suitable peptides include, but are not limited to, e.g., SEQ ID NO:9, SEQ ID NO:21, SEQ ID NO:23, SEQ ID NO:24, and SEQ ID NO:26.

The collagen mimetic peptides of the disclosure self-assemble into a collagen assembly. The collagen assembly comprises a triple strand helix assembly comprising a first, second and third strand containing multiple peptides. In some embodiments, the collagen assembly is human scale. In some aspects, the first, second and third strand of the collagen are associated by interstrand interactions, for example, but not limited to, interstrand salt bridges.

"Collagen" as used herein, refers to the natural extended triple-helical proteins that make up collagen fibers and fibrils.

"Human scale collagen" refers to synthetic collagen assemblies that are assembled from the self-assembling collagen peptides to resemble the approximate length and structure of naturally occurring human collagen. In some embodiments, the human scale collagen assembles into fibrillar collagen assemblies. In some embodiments, the human scale collagen assemblies comprise at least about 900 residues per strand, preferably about 950 residues, alternatively about 1000 residues per strand. In some embodiments, the human scale collagen assemblies comprise strands of about 100 nm in length, more preferably about 300 nm (0.3 μm) in length.

In some embodiments, the collagen assemblies form a collagen hydrogel. A collagen hydrogel is capable of swelling and retaining a significant fraction of water within its structure, but does not dissolve in water.

In some embodiments, the collagen hydrogel has an average molecular weight of about 100,000 or less, capable of being swollen by water over a wide range of water contents ranging from about 30 percent to 1000 percent and higher while possessing useful properties for specific end product uses. Methods of preparing a hydrogel from the collagen assemblies produced by the methods described herein are known in the art, for example as described in Example 3.

Suitable collagen assemblies to make hydrogels are disclosed herein, and include, but are not limited to SEQ ID NO: 35 (OKDO), SEQ ID NO: 28 (OKD2), and SEQ ID NO: 2 (OKD) among others.

Figure 1D:
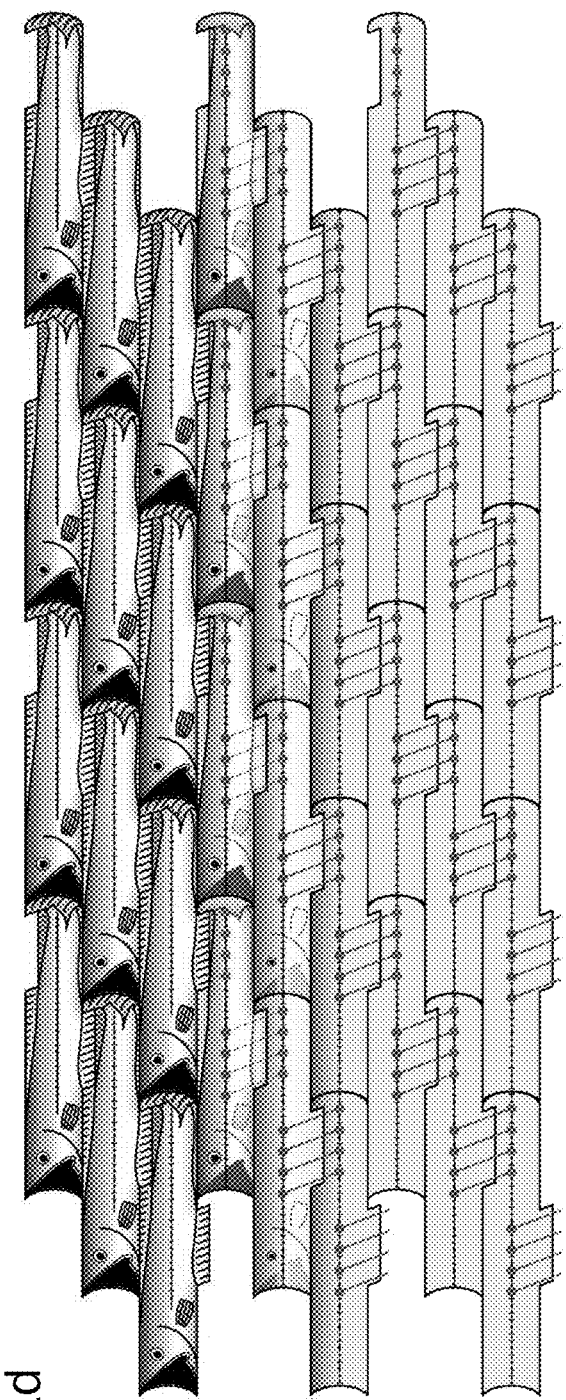
FIG. 1d depicts the principles of plane geometry that inspire artistic tessellations can also inspire the design of a peptide that forms a symmetric assembly around the triple-helical axis, enforced by salt bridges.
Figure 1E:
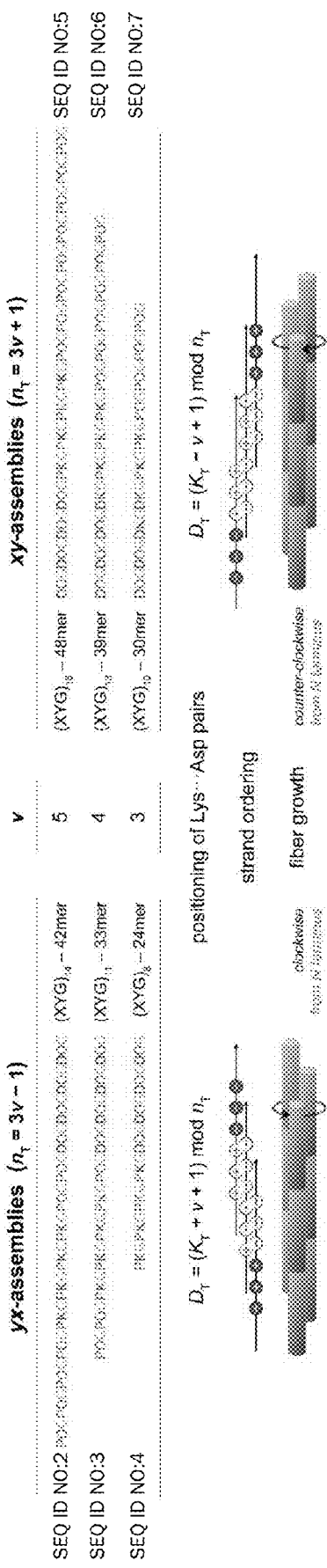
FIG. 1e depicts the design rules for the symmetric assembly of CMPs. The two classes of symmetric assembly require different relationships between $K_T$ and $D_T$, which are positions of XaaYaaGly-units that host Lys and Asp residues of an interacting Lys • • • Asp pair to ensure symmetric strand association. The examples have four Lys • • • Asp pairs per CMP.

In some embodiments, the equations in FIG. 1e provide guidance on identifying positioning of the K and D(/E) residues on a peptide so that they support and/or stabilize symmetric assembly. If the K and D(/E) residues are not paired this way, they will not be able to form salt bridges in a symmetric assembly.

The peptides (or collagen mimetic peptides) of the present disclosure allow for the formation of a polyproline-II helix. In some embodiments, the sequence of the peptide comprises a Gly at every third position, providing a sequence of Xaa-Yaa-Gly. In some embodiments, Xaa and Yaa can be selected from any amino acid. In some non-limiting embodiments, Xaa is selected from proline (Pro, P), aspartic acid (Asp, D), or glutamic acid (Glu, E) and Yaa is selected from proline (P), hydroxyproline (Hyp, 0), lysine (Lys, K) or (2S, 4R) 4-fluoroproline (Flp). In some embodiments, proline is sometimes used in both the Xaa and Yaa positions in collagen-mimetic strands.

For example: For a peptide where $n_T=14$, if you want to place a K residue within the 6$^{th}$ XaaYaaGly-repeat on the peptide ($K_T=6$), you have:

```
                                          (SEQ ID NO: 44)
XaaYaaGly XaaYaaGly XaaYaaGly XaaYaaGly

XaaYaaGly XaaKGly XaaYaaGly XaaYaaGly

XaaYaaGly XaaYaaGly XaaYaaGly XaaYaaGly

XaaYaaGly XaaYaaGly
```

$n_T=14=(3v-1)$ points to an yx-type of assembly with $v=5$ (i.e. FIG. 1e, left column), and using the equation there, you get $D_T=(K_T+v+1)$ mod $n_T=(6+5+1)$ mod $14=12$. Thus, you need to pair the Lys residue at $K_T=6$ with a Asp residue at the 12$^{th}$ XaaYaaGly-unit on the peptide:

```
                                          (SEQ ID NO: 45)
XaaYaaGly XaaYaaGly XaaYaaGly XaaYaaGly

XaaYaaGly XaaKGly XaaYaaGly XaaYaaGly
```

```
                           -continued
XaaYaaGly XaaYaaGly XaaYaaGly DYaaGly

XaaYaaGly XaaYaaGly
```

Figure 1F:
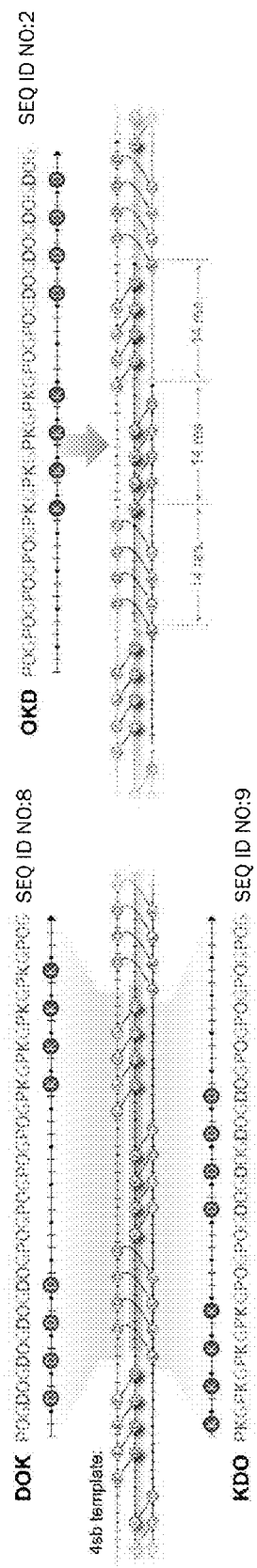
FIG. 1f depicts the symmetric assembly of 4sb-derived peptides. DOK, KDO, and OKD peptides are shown on the 4sb-template, highlighted in red, green, and blue, respectively. The perfect charge-pairing and uniform 14-residue interstrand stagger ensured by the symmetry rules are demonstrated with the OKD assembly.

FIG. 1f demonstrates that this pair forms a salt bridge in OKD assemblies.

These equations can also be used for other interstrand interactions besides Lys-Asp salt bridges. For example, these equations also describe where to install Hcy and Cys residues for disulfide bridging CMPs in a way to support symmetric assembly, but in that case the equations need to be modified slightly:

| yx-assemblies | xy-assemblies |
|---|---|
| $Hcy_T = (Cys_T + v) \bmod n_T$ | $Hcy_T = (Cys_T - v) \bmod n_T$ |

The "+1" is gone because, unlike Lys-Asp pairs, which are positioned one XaaYaaG-unit apart on the triple helix, Hcy-Cys bridges are between adjacent Xaa and Yaa residues.

Methods of determining the structure of the collagen assemblies are known in the art, and include, but are not limited to, circular dichroism (CD), analytical ultracentifugation (AUC), transmission electron microscopy (TEM), and dynamic light scattering (DLS).

In some aspects, Xaa is Pro and Yaa is Pro or Hyp (hydroxyproline). In some aspects, Xaa is Asp and Yaa is Lys.

"Self-assembling" peptides/collagen mimetic peptides or "self-assembly" refers to the ability of the peptides to assemble themselves spontaneously via specific, interstrand interactions between the peptides themselves to form a larger higher order functional unit of the tripeptide helical structure of collagen, without external direction.

A "higher order functional unit" or "unit" refers to a larger higher order component of the triple helical structure of collagen comprising at least two collagen mimetic peptides, for example a dimer (two peptides associated via interstrand interaction), trimer (three peptides associated via interstrand interaction), or any number of multimers, for example, n-mer (n-peptides associate via interstand interactions to form two or three strands, wherein n is a positive integer), etc. The term "multimer" can be used interchangeably with the term "unit" herein.

"Interstrand interactions" refer to the chemical interaction between two peptides. A chemical interaction includes, but is not limited to, a covalent bond (e.g. disulfide bond), a non-covalent interaction (e.g. salt bridge), or a chelation (e.g. a metal-ligand interaction). Suitable interstrand interactions include, but are not limited to, salt bridges, disulfide bonds, metal-binding sites, etc.

As depicted in FIG. 7b, the peptides self-assemble to form symmetric collagen assemblies. Symmetric assembly allows for the assembly of the peptides in any suitable order which do not form the higher-order structures (e.g. thick bundles) seen in peptides of the prior art. The self-assembly of peptides allows for the formation of the three strands of the triple helical collagen assembly, wherein each strand is offset from its neighboring strand by an $n_T$-residue offset.

In some embodiments, a first peptide associates with a second peptide with an $n_T$-residue offset. The first and second peptide can further associate with a third strand. A first and second peptide can associate by interstrand interactions to form a unit which forms the beginning of the first and second strand. Additional peptides or units can associate through interstrand interactions to initiate the third strand or elongate the first or second strand.

For example, a first and second peptide can associate to form a dimer unit. Alternatively, a first and second unit may associate to form a multimer (if at least one unit is a multimer (e.g. a single peptide associates with a multimer or a multimer associates with a second multimer). In some embodiments, if one of the symmetrically-associated units is a dimer and the other a single peptide, the result would be a trimer. In another example, if one of the units is a symmetrically-assembled n-mer, and the other a symmetrically-assembled m-mer, the result would be a symmetrically-assembled (n+m)-mer (where n and m are integers). Thus, the assembly is not limited to any specific sequence of addition of single or multiply-associated peptides or units.

In an embodiment, a first peptide can associate with a second peptide and/or a third peptide to initially form a homodimer unit comprising two peptides prior to forming a homotrimer unit, or the three peptides may associate relatively simultaneously to form the homotrimer unit. In some embodiments a homodimer or homotrimer having sticky ends may associate with an existing single peptide or with another homodimer, homotrimer or multimer.

For the purposes of this disclosure "associate" or "association" between peptides is defined by the interstrand interaction leading to the formation of a unit having sticky ends (for example, a dimer or trimer).

Figure 10:
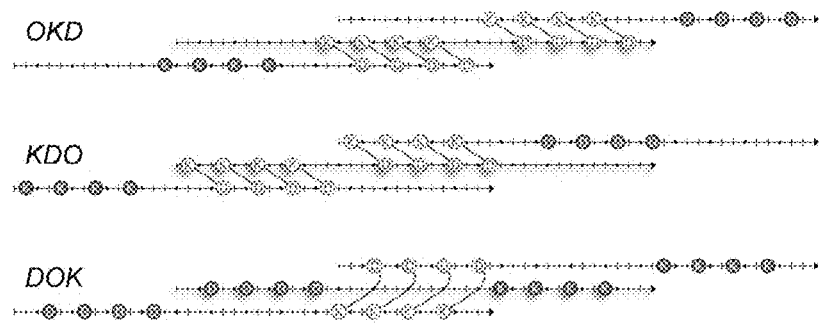
FIG. 10 depicts the salt-bridge propagation in 4sb-like assemblies. When assembled, OKD and KDO peptides form salt bridges with neighbors they interact most closely with, while DOK peptides do not.

In one embodiment, the collagen mimetic peptides assemble symmetrically to form a first homodimer or ultimately a homotrimer having sticky ends. A depiction of a homotrimer with sticky ends is depicted in FIG. 1b or FIG. 10. In some aspects, the first symmetrical homotrimer comprises a first, a second and a third collagen mimetic peptide, wherein at least two of the first, second and third peptides are stabilized by at least one interstrand interaction, for example, an interstrand salt bridge.

In some embodiments, a first symmetrically-assembled multimer joins a second symmetrically-assembled multimer. In further embodiments, the second symmetrical multimer comprises at least two joined symmetrical homodimers or homotrimers. In some embodiments, a plurality of symmetrical multimers are formed. In some embodiments, the plurality of symmetrical multimers assemble to form a symmetrical triple helical collagen assembly. In some embodiments, the number of bridges cross-linking the assembled peptide is dictated by the length of symmetrical multimers, for example, the number of lysine-aspartic acid interactions to form salt bridges. In some embodiments, the nature of the interactions (such as the number of salt bridges) that interconnect the peptides in the assembly is directed by the length of those peptides.

In some embodiments, a first, second and third peptide are each stabilized with a neighboring strand by at least one interstrand interaction, for example, a salt bridge. In some aspects, the first, second and third strands are stabilized by at least two interstrand interactions (e.g. salt bridges). In some embodiments, the first, second and third strands are stabilized by at least three interstrand interactions, alternatively at least four interstrand interactions, alternatively at least five interstrand interactions, alternatively, at least 6 interstrand interactions, alternatively, at least 7 interstrand interactions, etc.

Suitable interstrand interactions are known to one skilled in the art. For example, suitable interstrand interactions refer to a salt bridge, a disulfide bond, or the like.

In some embodiments, the at least one interstrand interaction is an interstrand salt bridge. In some instances, the interstrand salt bridge cross-links at least one lysine residue in the Yaa position on the first peptide or strand and at least one aspartic acid residue in the Xaa position at a three residue offset on the second peptide or strand occupying the next register. In some further instances, a second at least one salt bridge links at least one lysine residue in the Yaa position on the second peptide or strand and at least one aspartic acid residue in the Xaa position at a three residue offset on the third peptide or peptide occupying the next register. In yet a further instance, a third at least one salt bridge links at least one lysine residue in the Yaa position on the third peptide or strand and at least one aspartic acid residue in the Xaa position at a three residue offset on the first peptide or strand occupying the next register. For the purposes of this disclosure, the terms "offset" and "shift" are used interchangeably.

As collagen is a triple helical structure comprising a first, second and third strand, neighboring strands are referred to as the strand in the previous or the next register. In determining a three residue offset, it refers to the amino acid that is three residues down on the peptide of the strand in the next register within the triple helix (for example, a first strand may contain a lysine residue at the Yaa position on the first strand, which forms an interstrand salt bridge with either aspartic acid residue in the Xaa position at a three residue offset on the second strand in the triple helical collagen assembly) as shown in at least FIG. 1a or 1f.

In some embodiments, greater than about 90% of the available lysine residues and available aspartic acid residues are linked by an interstrand salt bridge. In some embodiments, greater than 95% of the available lysine residues and available aspartic acid residues are linked by an interstrand salt bridge. In other embodiments, all or substantially all of the available lysine residues and available aspartic acid residues are linked by an interstrand salt bridge. The number of lysine residues and aspartic acid residues within a collagen mimetic peptide may vary depending on its sequence. In some embodiments, the collagen mimetic peptides contain at least one lysine and one aspartic acid. In other embodiments, the collagen mimetic peptide contains at least two lysines and two aspartic acids.

In some embodiments, the first, second and third strand can associate with additional strand(s) and/or collagen mimetic peptides to elongate any one of the first, second or third strands of the collagen assembly forming a triple helical collagen assembly.

In the formation of the triple helical structure, sticky ends are formed. "Sticky ends" refer to the overhang on each peptide/unit that allow for association of additional peptides into the triple helical structure. Each individual peptide does not contain sticky ends. Any assembly of two peptides will have two sticky ends. Any assembly/unit of three (3) or more peptides (e.g., multimer) has 4 sticky ends. Each unit/assembly of two peptides has two sticky ends, one at the N-terminal and one at the C-terminal ends of the unit/assembly. For example, between two peptides/assemblies that associate, the terminal peptide(s) on the two sides will gain a new neighbor, with which they overlap $2 \times n_T$ residues, which forms a sticky end.

In some embodiments, a first collagen mimetic peptide or strand may associate with a second collagen mimetic peptide or strand to form a homodimer having at least one sticky end, and preferably two sticky ends, one formed at a first end of the homodimer and one formed at a second end of the homodimer. The first and second peptide or strand may associate with a third peptide or strand to form a homotrimer having at least two, and preferably four sticky ends, two formed at a first end of the homotrimer and two formed at a second end of the homotrimer, as shown in at least FIG. 1b. Additional collagen-mimetic peptides or strands may join at least one of the first, second (homodimer) or third (homotrimer) peptides via the sticky end(s) to elongate the self-assembling symmetrical collagen assembly. For example, a fourth mimetic peptide or strand may join the homodimer or homotrimer via any of the available sticky ends to elongate the triple helix. In addition to single peptide or strands, previously formed homodimers or homotrimers may join the current homodimers or homotrimers via any available sticky end. The numbering or ordering of the mimetic peptides or strands is not to suggest a specific order of assembly of the peptides. Symmetrical self-assembly of the peptide or strands may occur in any order to form a homotrimer, ultimately forming a triple-helical collagen assembly that may be further self-assembled into a collagen assembly. The symmetrical self-assembly is not limited to dimers and trimers, as any multimer may participate in the elongation of the triple helical structure in a similar manner as the dimer and trimers described herein.

In some embodiments, at least two collagen mimetic peptides self-assemble to form a unit. In some embodiments each associated collagen mimetic peptide in a unit comprises a first sticky end and a second sticky end in the case of a homodimer and first, second, third and fourth sticky ends in the case of the homotrimer or other multimer (containing 3 or more peptides). A first unit may join with a second unit by joining via the sticky ends formed in each the first and the second unit. At least two collagen mimetic peptides may self-assemble by joining a first sticky end of a first collagen mimetic peptide unit to a second sticky end of a second collagen mimetic peptide unit. In some embodiments, the method further comprises joining a second sticky end of the first collagen mimetic peptide unit to a second sticky end of a third collagen mimetic peptide unit, thus forming a symmetrically assembled triple-helical collagen assembly elongating at each end of the original unit. Elongation may also proceed in either or both directions, from either the first end or the second end of the unit, or combinations thereof, and not necessarily at the same rate, or if in different directions, the same number of units. In some embodiments, a first single collagen mimetic peptide may symmetrically self-assemble to an existing unit by joining at a sticky end of the existing unit. Single peptides or strands, and/or units may join via the sticky ends thereby elongating the collagen assembly. In some embodiments, two or more units assemble to form the collagen assembly. In other embodiments, an additional collagen mimetic peptide joins the first, second or third strand of the unit to elongate the first, second or third strand.

The orientation of the first, second, third and fourth sticky ends used herein for the units are for illustrative purposes and are not to specify a specific orientation. It can be understood by one skilled in the art that each peptide has a first and second end, which may join with other collagen mimetic peptides by joining with a pre-formed sticky end of an existing unit to elongate the collagen assembly, and also associate with other collagen mimetic peptides in one and/or two neighboring strands, for example, a first collagen mimetic peptide associates via interstrand salt bridges (or possibly other interactions) with a second peptide to form a dimer, and the first and second peptides associate with a third collagen mimetic peptide to form a homotrimer. The peptides or units self-assemble in a symmetrical fashion to form a triple-helical collagen assembly. One skilled in the art would understand that the direct order of additional peptide elongation may vary to arrive at the collagen assembly. In some embodiments, the plurality of collagen mimetic peptides assemble to form a symmetrical triple helical collagen assembly. The number of interstrand interactions, for example, salt bridges contained within the assembly depends of the length of the collagen mimetic peptides and, in the case of salt bridges, the number of lysine and aspartic acid interactions between two different strands of the triple helical collagen assembly or number of cysteines for disulfide bonds. For example, a suitable collagen mimetic peptide assembly contains about 4 salt bridges per about 14 residues.

In some embodiments, the self-assembling collagen mimetic peptides comprising Xaa-Yaa-Gly tripeptide repeats, wherein the number of tripeptide repeats ($n_T$) is $3v\pm1$, wherein v is a positive integer from 1 to 10, wherein the collagen mimetic peptides assemble with an $n_T$-residue offset between neighboring strands of the collagen assembly.

In some embodiments, v is a positive integer from 1 to 10, preferably 3 to 7. In some embodiments, v is 3, in other embodiments, v is 4, in other embodiments, v is 5, in other embodiments, v is 6. In a preferred embodiment, v is 5.

In some embodiments, the number of tripeptide repeats ($n_T$) is $3v+1$, wherein the peptide is n residues in length, wherein $n=n_T \times 3$. In some instances, $n_T$ is 4, 7, 10, 13, 16, 19, 22 and n is 12, 21, 30, 39, 48, 57, 66, respectively. In a preferred embodiment, v is 5 and $n_T$ is 16 and n is 48. In another preferred embodiment, v is 4 and $n_T$ is 13 and n is 39.

In another embodiment, the number of tripeptide repeats ($n_T$) is $3v-1$. In some instances, $n_T$ is 2, 5, 8, 11, 14, 17, 20, 23, 26. In a preferred embodiment, v is 5 and $n_T$ is 14 and n is 42. In another preferred embodiment, v is 4 and $n_T$ is 11 and n is 33.

In some embodiments, the Xaa-Yaa-Gly tripeptide repeats comprises Xaa-Yaa-Gly tripeptide repeats of PKG, DOG, POG or combinations thereof. In other embodiments, the Xaa-Yaa-Gly tripeptide repeats are selected from the group consisting of POG, PKG, DOG, DKG and combinations thereof (wherein P is Proline (Pro), K is Lysine (Lys), 0 is hydroxyproline (Hyp), D is aspartic acid (Asp), and G is Glycine (Gly)). Non-limiting examples of suitable collagen mimetic peptides are described in Table 2, for example SEQ ID NO: 2-10, 12, 14-18, 22, 27-37. In some embodiments, the collagen mimetic peptides are selected from the group consisting of SEQ ID NO: 2 (OKD), SEQ ID NO: 28 (OKD2) and SEQ ID NO: 35 (OKDO). In some embodiments, the collagen mimetic peptide is SEQ ID NO: 24 (KDO), SEQ ID NO:8 (DOK), SEQ ID NO: 9 (KDO), SEQ ID NO: 2 (OKD), SEQ ID NO: 28 (OKD2), SEQ ID NO: 35 (OKDO), or SEQ ID NO: 36 (KDO2). In some embodiments, the collagen assemblies comprise collagen mimetic peptides of SEQ ID NOs: 2-10, 12, 14-18, 22, 27-37 or combinations thereof.

In one embodiment, the collagen assemblies comprise two different collagen mimetic peptides, for example two or more collagen mimetic peptides selected from the group consisting of SEQ ID NOs: 2-10, 12, 14-18, 22, 27-37.

In some embodiments, the collagen mimetic peptides comprise tripeptides of POG, PKG, DOG, and combinations thereof.

In a further embodiment, the disclosure provides a synthetic symmetrical triple helical collagen assembly comprising collagen mimetic peptides comprising:

$$(POG)_n(PKG/DOG)_m(POG/DKG)_p(DOG/PKG)_q(POG)_r \quad \text{(SEQ ID NO: 46)}$$

wherein "/" signifies one or the other tripeptide, but not both (for example, $(PKG/DOG)_m$ signifies $(PKG)_m$ or $(DOG)_m$), and wherein n, m, p, q and r are selected from 0 or are independently selected from a positive integer, e.g. 1-10 and wherein n+m=n+m+p+q+r=3v±1>0. In some aspects, $n_T$>3 or $n_T$>6. In some preferred embodiments, m=q, and preferably m and q are not 0. In some embodiments, n, m, p, q and r are each a positive integer, for example, a positive integer selected from 1-10.

In some embodiments, the sequence comprises $(PKG)_m$ and $(DOG)_q$, wherein m and q are the same, and wherein m and q are a positive integer, for example 1-10.

In some embodiments, the collagen assembly comprises peptides selected from one of the following sequences:

$$(POG)_n(PKG)_m(POG)_p(DOG)_q(POG)_r; \quad \text{(SEQ ID NO: 47)}$$

$$(POG)_n(PKG)_m(DKG)_p(DOG)_q(POG)_r; \quad \text{(SEQ ID NO: 48)}$$

$$(POG)_n(DOG)_m(POG)_p(PKG)_q(POG)_r; \quad \text{(SEQ ID NO: 49)}$$

or $$(POG)_n(DOG)_m(DKG)_p(PKG)_q(POG)_r, \quad \text{(SEQ ID NO: 50)}$$

wherein n, m, p, q, and r are selected from 0 or a positive integer, e.g. 1-10 and wherein $n_T$=n+m+p+q+r=3v±1>0. In some embodiments, m=q. In some embodiments, m=q, and m and q are an integer from 1-10. In some aspects, only one of n, p, or r are 0. In some aspects, m=q.

In some embodiments, n, m, p, q and r are not 0, and are selected from 1-10.

In some embodiments, one of n, p, or r are 0, but the others are positive integers.

In some embodiments, n, m, p, q and r are selected from 2-6, preferably from 2-4.

In some embodiments, n, m, p, q and r are independently selected from 2-4.

In some embodiments, the collagen assembly comprises $(POG)_n(PKG)_m(POG)_p(DOG)_q(POG)_r$ (SEQ ID NO:47), wherein n, m, p, q, and r are selected from 0 or a positive integer, e.g. 1-10 and wherein $n_T$=n+m+p+q+r=3v±1>0. In some embodiments, m=q. In some embodiments, m=q, and m and q are an integer from 1-10. In some aspects, only one of n, p, or r are 0. In some aspects, none of n, m, p, q or r are 0. In some embodiments, m=q.

In some embodiments, the collagen assembly comprises peptides selected from one of the following sequences:
$(POG)_n(PKG)_m(DKG)_p(DOG)_q(POG)_r$ (SEQ ID NO:48); wherein n, m, p, q, and r are selected from 0 or a positive integer, e.g. 1-10 and wherein $n_T$=n+m+p+q+r=3v±1>0. In some embodiments, m=q. In some embodiments, m=q, and m and q are a integer from 1-10. In some aspects, none of n, m, p, q, or r are 0 and are selected from 1-10. In other aspects, only one of n, p, or r are 0. In some aspects, m=q.

In some embodiments, the collagen assembly comprises peptides selected from one of the following sequences:
$(POG)_n(DOG)_m(POG)_p(PKG)_q(POG)_r$ (SEQ ID NO:49); wherein n, m, p, q, and r are selected from 0 or a positive integer, e.g. 1-10 and wherein $n_T$=n+m+p+q+r=3v±1>0. In some embodiments, m=q. In some embodiments, m=q, and m and q are a integer from 1-10. In some aspects, none of n, m, p, q, or r are 0. In other aspects, only one of n, p, or r are 0. In some aspects, m=q.

In some embodiments, the collagen assembly comprises peptides selected from one of the following sequences:
$(POG)_n(DOG)_m(DKG)_p(PKG)_q(POG)_r$ (SEQ ID NO:50), wherein n, m, p, q, and r are selected from 0 or a positive integer, e.g. 1-10 and wherein $n_T$=n+m+p+q+r=3v±1>0. In some embodiments, m=q. In some embodiments, m=q, and m and q are an integer from 1-10. In some aspects, none of n, m, p, q, or r are 0. In other aspects, only one of n, p, or r are 0. In some aspects, m=q.

In some embodiments, the collagen mimetic peptides comprise:

$$(POG)_n(PKG)_m(POG)_p(DOG)_q(POG)_r \quad \text{(SEQ ID NO: 47)}$$

wherein n=0 or 1; m=3 or 4; p=2, 3 or 4; q=3 or 4 and r=2, 3 or 4.

In some embodiments, the collagen mimetic peptides comprise:

$$(POG)_n(DOG)_m(POG)_p(PKG)_q(POG)_r \quad \text{(SEQ ID NO: 49)}$$

wherein n, m, p, q and r are independently selected from 1, 2, 3 or 4.

The plurality of collagen mimetic peptides assemble into a symmetrical triple helix containing three strands in which each strand is at least about 150 residues to about at least 1200 residues in length, alternatively about 300 residues to at least about 1000 residues in length, alternatively about 400 residues to about 900 residues in length, alternatively about 500 residues to about 900 residues in length. The length of each strand may be at least about 150 residues, alternatively about 200 residues, alternatively about 250 residues, alternatively about 300 residues, alternatively about 400 residues, alternatively about 500 residues, alternatively about 550 residues, alternatively about 600 residues, alternatively about 650 residues, alternatively about 700 residues, alternatively about 750 residues, alternatively about 800 residues, alternatively about 850 residues, alternatively about 900 residues, alternatively about, 950 residues, and contains any number of residues in-between, for example, 575 residues, 580 residues, 590 residues, etc.

In some preferred embodiments, the plurality of collagen mimetic peptides assemble into a symmetrical triple helix wherein each strand of the helix comprises at least about 500 residues. In some embodiments, each strand of the helix comprises at least about 900 residues. In some embodiments, the plurality of collagen mimetic peptides assemble into human scale collagen triple helices. Human scale collagen triple helices are at least about 500 residues in length, more preferably at least about 900 residues in length.

In some embodiments, the plurality of collagen mimetic peptides assemble into a symmetrical triple helix of at least about 200 nm in length. In other embodiments, the plurality of collagen mimetic peptides assemble into a symmetrical triple helix of at least about 300 nm (≥0.3 μm) in length. In some embodiments, the strands of the triple helical collagen are at least about 45 nm in length, alternatively at least about 60 nm in length. In some embodiments, the collagen assembly peptides are at least about 300 nm to 400 nm in length.

The methods described herein produce collagen mimetic peptides that form a single stranded triple helical collagen assembly (single fiber). The diameters of the fibers are consistent with single triple helices that have not been shown before for synthetic peptides of the length contemplated herein. In some embodiments, the diameter of the triple helical collagen assemblies are from about 1 to about 4 nm, in some embodiments, the diameter is from about 2 to about 4 nm. These diameters of the synthetic triple helical collagen assemblies are similar to the single triple helices of natural collagen. For example, the Examples demonstrate the thickness of the fibers formed in the present invention. Not to be bound by any theories, but it is believed that the symmetrical design of the collagen mimetic peptides allows for all the charged residues to be paired giving the strands a neutral charge, and thus the product does not have any polar (+ or −) regions that would attract and bind to charged peptides to form aggregates of fibers.

In some embodiments, the plurality of collagen mimetic peptides assemble into symmetrical triple helixes that have fibers with a diameter from about 1-10 nm, preferably from 1-8 nm, more preferably from 1-4 nm.

The methods of the present invention provide symmetrical triple helical collagen assemblies/strands that are more stable (have higher Tm), have diameters consistent with single strands of collagen triple helixes (e.g. from about 1 nm to about 4 nm diameter) as opposed to random assemblies, and the single fibers are exceptionally long for synthetically made collagen triple helices. Applicant submits there are surprising advantages of using the symmetrical collagen mimetic peptide assembly method described herein over the prior methods in the art.

In some embodiments, the collagen mimetic peptides are designed to reduce blunt end association between the pluralities of collagen mimetic peptides. Methods of destabilizing blunt-end association are known to one skilled in the art. For example, in a non-limiting example, Xaa is proline (Pro, P) and Yaa is lysine (Lys, K) in the central portion of the collagen mimetic peptide to reduce blunt end association. In another example, the collagen mimetic peptides contain Yaa repeats of hydroxyproline (Hyp, 0) at the termini of the collagen mimetic peptide to reduce blunt end association. In order to reduce blunt end association, the collagen mimetic peptides are designed to provide repulsive interstrand interactions that reduce the likelihood of blunt-end association between the pluralities of collagen mimetic strands.

In some embodiments, the symmetrical triple helical collagen assembly has a melting temperature (Tm) of greater than about 37° C. In some embodiments, the symmetrical triple helical collagen assembly has a Tm of greater than about 45° C. In some embodiments, the symmetrical triple helical collagen assembly has a Tm of greater than about 50° C. In some embodiments, the symmetrical triple helical collagen assembly has a Tm of about 46° C., of about 47° C., of about 48° C., of about 49° C., of about 50° C., of about 51° C., of about 52° C., of about 53° C., of about 54° C., of about 55° C., of about 56° C., of about 57° C., of about 58° C., of about 59° C., of about 60° C. In some embodiments wherein the symmetrical helical collagen assembly comprises disulfide linked dimers, the Tm is about 55° C. to about 60° C. In some embodiments, the collagen mimetic strands have a Tm from about 37° C. to about 60° C., alternatively from about 45° C. to about 60° C.

In some embodiments, a synthetic symmetrical triple helical collagen assembly is provided. The symmetrical triple helical collagen assembly may comprise a plurality of self-assembling collagen mimetic peptides comprising Xaa-Yaa-Gly tripeptide repeats, wherein the number of tripeptide repeats ($n_T$) is $3v\pm1$, wherein v is a positive integer, wherein the peptide is n residues in length, wherein $n=n_T\times3$ with an $n_T$ offset; wherein the collagen mimetic peptides self-assemble to form the symmetrical triple helical collagen assembly. In one embodiment, the synthetic triple helical collagen assembly contains at least one interstrand salt bridge linking at least one lysine residue in the Yaa position on a first strand and at least one aspartic acid residue in the Xaa position at a three residue offset on a second strand occupying the next register. In yet a further aspect, this synthetic triple helical collagen assembly contains a second salt bridge linking at least one lysine residue in the Yaa position on the second strand and at least one aspartic acid residue in the Xaa position at a three residue offset on a third strand occupying the next register. In yet a further aspect, this synthetic triple helical collagen assembly contains a third salt bridge linking an at least one lysine residue in the Yaa position on the third strand and at least one aspartic acid residue in the Xaa position at a three residue offset on the first strand occupying the next register.

In some embodiments, the collagen assemblies may be functionalized with any desired moiety. As a non-limiting example, lysine may be included in the sequence of the collagen assemblies so that fluorophores, therapeutics or other cargo can be attached to the growing assembly at the NC atom. However, Lys is not the only residue that could facilitate such attachment, and other side-chains could be used as well. By way of example only, side chains containing alkenes, alkynes, aldehydes, azides, and thiols could be all be used for this purpose.

Accordingly, any amino acid residue capable of being functionalized may be included at the Xaa or Yaa position to facilitate functionalizing the collagen-mimetic peptide, so long as the functionalization does not disrupt the ability of the collagen assembly to form a triple helical structure. The amino side chain of lysine or any other amino acid residue capable of being functionalized may be functionalized with a desired moiety using standard synthetic techniques known in the art, so long as the functionalization does not disrupt the ability of the collagen assembly to form the triple helical structure. By way of example only, a cysteine may be provided and functionalized at the terminal thiol, as desired, using methods known in the art.

In some embodiments, the symmetric collagen assembly comprises collagen mimetic peptides containing at least one cysteine or homocysteine that forms at least one disulfide bond between the collagen mimetic peptides in the symmetric collagen assembly, see, for example, collagen assemblies comprising SEQ ID NOs: 29 and 30, SEQ ID NOs:31 and 32, or SEQ ID NOs: 33 and 34. In this embodiment, the cysteine may be found at the Yaa position and homocysteine at the Xaa position demonstrated in the noted sequences.

In some embodiments, the collagen assemblies may include a binding sequence within the collagen mimetic peptides, for example, but not limited to, an integrin binding sequence. Other suitable binding sequences may also be incorporated, so long as the ability of the triple helical structure of the collagen is not disrupted from formation of collagen assembly.

The disclosed collagen assemblies have a variety of potential applications, including, without limitation, in biomaterials used for tissue repair and/or tissue engineering. In some embodiments, the collagen assemblies can be used for wound dressing and wound repair.

As a non-limiting example, the disclosed collagen assemblies may be used to treat wounded tissue or to facilitate the delivery of therapeutic agents or cytoactive factors to acute or chronic tissue wounds. Compositions containing collagen assemblies may be used for wound dressing, in dural closures, for reinforcement of compromised tissues, and in guided tissue regeneration. Such compositions can be used as vehicles for the sustained release of pharmaceuticals or therapeutic agents, including without limitation antibiotics or growth factors, such as recombinant human growth factor (hGF), platelet-derived growth factor (PDGF), fibroblast growth factor (FGF), or neuropeptides, such as Substance P. Therapeutics, such as growth factors, can be attached to self-assembling linked-dimers to aid in wound healing.

For example, a peptide that carries a growth factor may be mixed with peptides not carrying a factor to form a hydrogel. The ratio of the mixture will determine the desired dose within the collagen hydrogel that can be administered to a subject.

As another non-limiting example, the disclosed collagen assemblies may be used in cell culture scaffold compositions for both in vivo and in vitro applications. For instance, a non-limiting example is the use of the collagen assemblies for repair or regeneration of cartilage in a joint, for example, a knee, shoulder, ankle, wrist, shoulder joint or the like. In some embodiments, non-limiting examples of use of the disclosed collagen assemblies are for hydrogels to be used as substrates for cell-culture work, including, for example, stem-cell culture.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

This specification includes the sequence listing that is concurrently filed in computer readable form. This sequence listing is incorporated by reference herein.

EXAMPLES

Example 1: Symmetric Assembly Design of Human Scale Collagen Triple Helices

FIG. 1a-f depict the design of symmetric CMP self-assemblies. The recent discovery of a stabilizing "axial" salt bridge in the collagen triple helix has enabled CMP association to be controlled through peptide sequence. These salt bridges link a lysine residue (Lys; K) in the Yaa position and an aspartic acid residue (Asp; D) in the Xaa position three residues down (three residue "offset" on the strand occupying the next register (FIG. 1a)[22,23]. Hence, permutations of $(PKG)_4$, $(DOG)_4$, and $(POG)_4$ blocks within a 36-mer have been used as cationic, anionic, and neutral domains that weaken blunt-ended association while strengthening sticky-ended assembly of CMPs (FIG. 1b). The resulting constructs vary greatly in their morphology, some forming higher-order structures, such as hydrogels[19] and birefringent rods[21], and others remaining as amorphous aggregates[21]. This heterogeneity is partially attributable to the association of unpaired Lys and Asp residues with other strands or triple helices (e.g., FIG. 1c).

We reasoned that engaging all, or substantially all, Lys and Asp residues in interstrand salt bridges could ensure maximal stability for CMP hybridization and assembly, widen the energetic gap between the sticky- and blunt-ended associations, and limit unintended associations. We realized that such perfect pairing of charges is possible only if the design incorporates elements of symmetry. A "symmetric assembly" would require every peptide to engage in identical interactions with its neighbors, analogous to the tessellation of uniform tiles described by the geometer H. S. M. Coxeter[24] and depicted by the artist M. C. Escher[25] (FIG. 1d). Such symmetry would ensure that each CMP engages in an identical number of salt bridges, and would require that the same number of residues offset any two immediate neighbors in the assembly. Thus, the required sticky-ends are of uniform size across the assembly at n/3 residues for an n-residue CMP. This rule, in combination with the requirement for a single residue stagger between XaaYaaGly-repeats on neighboring strands, restricts peptides that are amenable to symmetric assembly to those that are 3v±1 XaaYaaGly-repeats in length, where v is a positive integer. For example, symmetric assemblies are therefore not possible for a 36-residue CMP ($n_T$=12 XaaYaaGly-repeats) (FIG. 2).

Sequences that satisfy symmetric assembly requirements fall into two distinct classes (FIG. 1e). The yx-class assembles through peptides of size $n_T$=3v−1 and accepts new building blocks in clockwise order around the triple-helical axis during N- to C-terminal growth, while peptides of size $n_T$=3v+1 (the xy-class) assemble counter-clockwise. Although v represents the number of XaaYaaGly-repeats that offset neighboring CMPs for both classes, the sign of the offset and ordering of strands differ. Thus, $n_T$=3v−1 assemblies favor the placement of PKG-repeats ahead of DOG-repeats on the peptide sequence, and vice versa. Among candidates that allow four fully paired Asp and Lys residues per CMP, we opted to study the 42-residue system (yx, v=5) as it enables segregation of charged blocks in the assembled state.

Figure 4A:
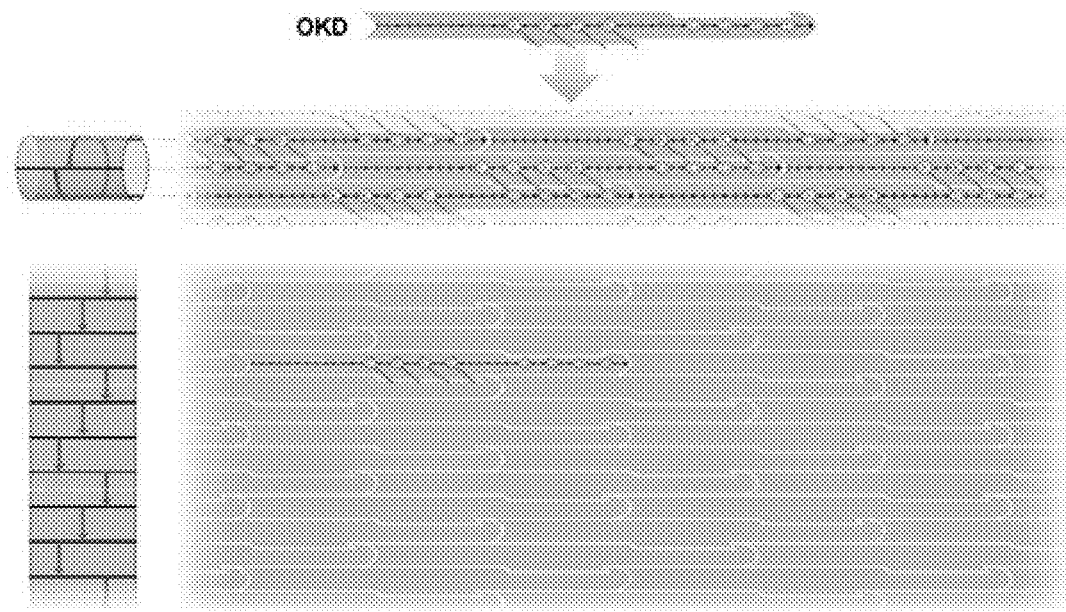
FIG. 4a depicts the tessellation of peptides in two dimensions and depicts the symmetric design of OKD self-assemblies ensuring identical interactions for every peptide and strand in the assembly. The resulting network of inter- and intrastrand interactions encompasses the triple helix completely, yielding a tessellation in two dimensions. This tessellation can be visualized through "peptide tiles" that encode the sequence and interactions of a peptide. Upon OKD self-assembly, these tiles tessellate around the central axis of the triple helix, satisfying all possible inter-peptide contacts. "Unrolling" this cylinder to cover a plane presents a tessellation of peptide tiles belonging to the plane symmetry group, p1.
Figure 4B:
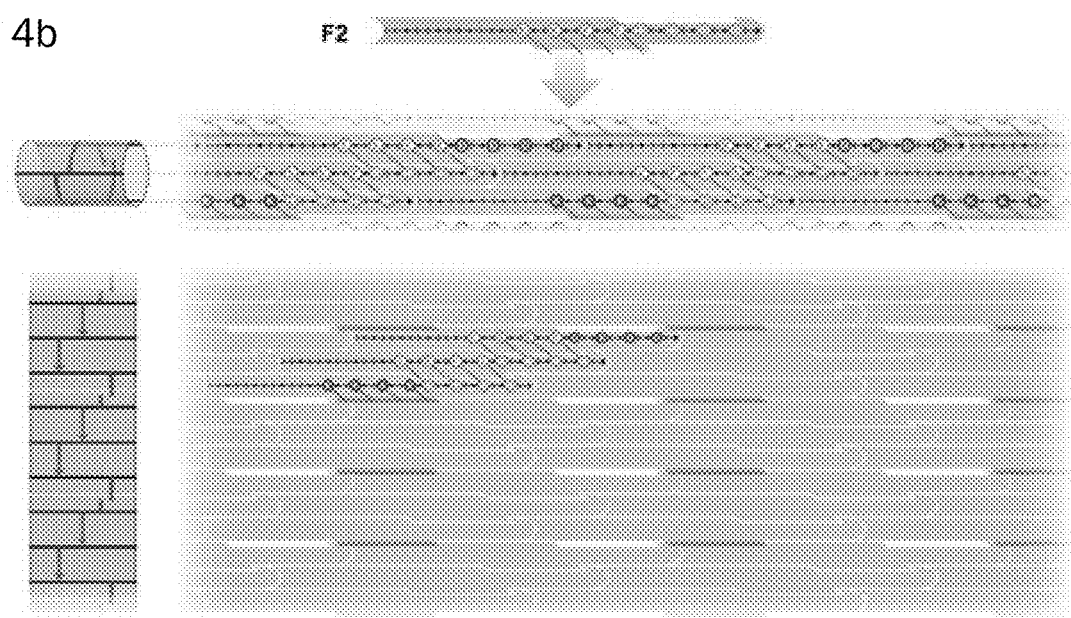
FIG. 4b depicts the F2 peptide cannot produce symmetric assemblies, and thus cannot form such tessellations.

The selected assembly can be interpreted as a homotrimer of three infinite strands, each offset by a 14-residue "super-stagger" with respect to its neighbors. We name this infinite homotrimer, which bears 4 salt bridges every 14 residues, the "4sb-template" (FIG. 10. Any 42-residue section taken out of this master template satisfies symmetric-assembly design requirements equally, and should be able to reestablish all contacts on the template upon assembly. We chose to synthesize and assess three 42-mers: 4sbG, 4sbG-KDO and 4sbG-OKD. These three peptides represent three extremes for charge placement on a 4sb-type peptide. In this example we refer to these peptides as DOK, KDO, and OKD, respectively (FIG. 1f). As intended, symmetric design provides identical chemical environments within the assembly for all three permutations, allowing uninterrupted CMP tessellation with fully paired Asp and Lys residues (FIG. 4).

Results

Figure 3A:
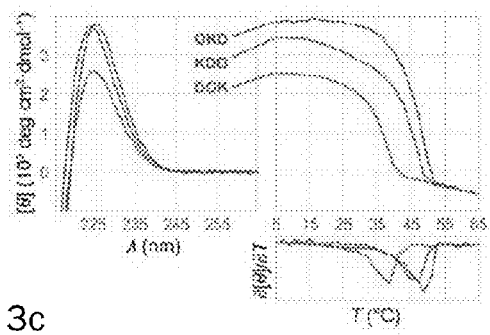
FIG. 3a depicts the CD spectra and thermal denaturation curves of 4sb-like CMP self-assemblies.
Figure 6:
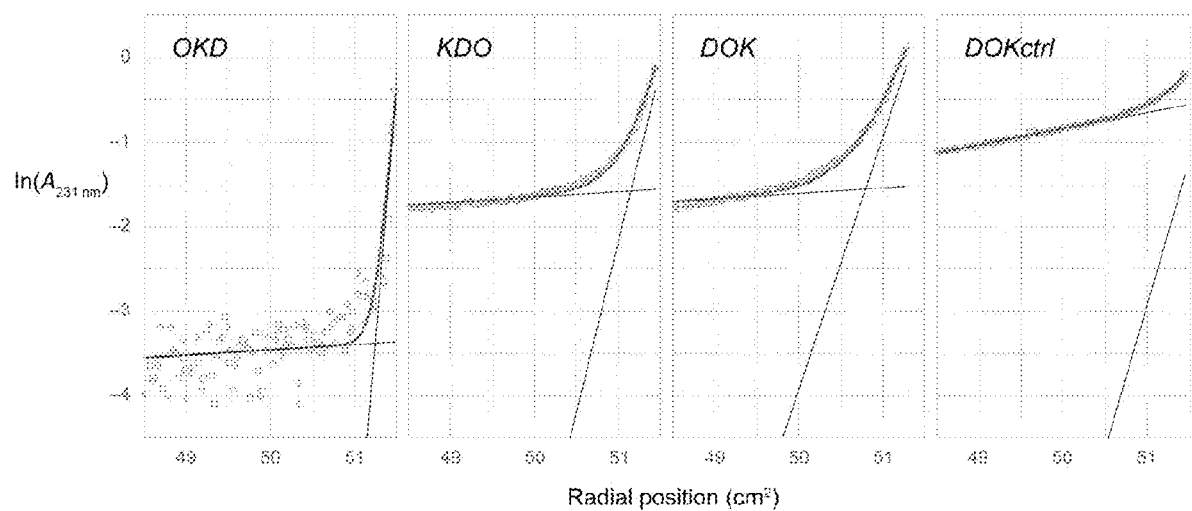
FIG. 6 depicts the AUC analysis of 4sb-like assemblies. Equilibrium gradients at 15 k rpm and 4° C. are shown (gray circles) with models that best explain the data. Here, the slope at any radial position is proportional to the weight-averaged molecular weight at that position in the centrifuge cell. A two-species model (red line) that includes a monomer and a multimer component (black lines) can describe patterns observed for OKD, KDO and DOK assemblies. Nonetheless, this model performs poorly for DOKctrl, necessitating a trimer+multimer model. Model (red) and components (black) shown are the 15 k rpm results of a fit to data at 8.8 and 15 k rpm.
Figure 8A:
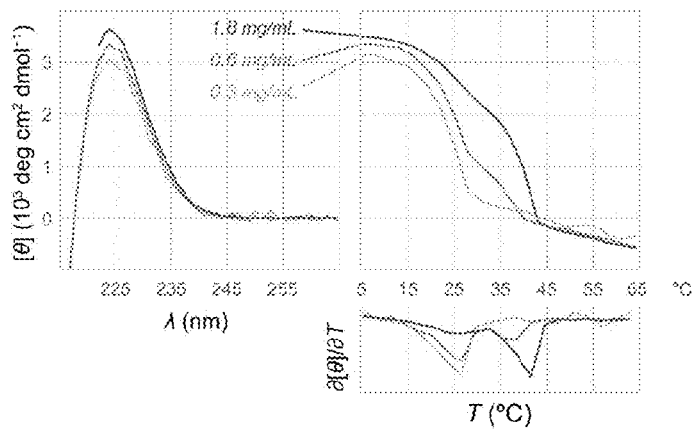
FIG. 8a depicts the CD spectra and temperature melts for F0 assemblies in 10 mM sodium phosphate buffer, pH 7.0, revealing concentration-dependent formation of presumed higher-order assemblies.
Figure 8B:
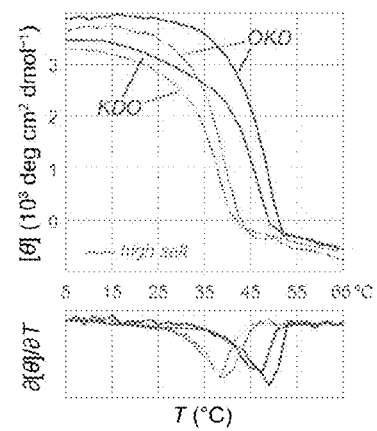
FIG. 8b depicts the temperature melts for OKD and KDO assemblies (0.6 mg/mL) in high (dashed) and low ionic-strength sodium phosphate buffer (solid lines) at pH 7.0.

We employed methods established previously for CMP synthesis[14], purification[26], and sample preparation[27,26]. Annealed peptides were not turbid and remained soluble within a 0.1-5 mg/mL range of concentration. Thermal denaturation experiments revealed "melting" temperatures ($T_m$) above 37° C. for all assemblies. All peptides displayed a strong circular dichroism (CD) signature for collagen at ~225 nm, indicative of triple-helix formation (FIG. 3a); self-assembly, confirmed by analytical ultracentrifugation (AUC), yields increasing size with increasing thermostability (FIG. 6). The DOK peptide, which keeps the (POG)$_4$ section mid-sequence, is the least stable permutation ($T_m$=38° C.), whereas the KDO and OKD peptides with negative and positively charged central sections form assemblies with higher $T_m$ values (46 and 49° C., respectively). The denaturation curves are increasingly cooperative for more stable peptides, displaying transitions reminiscent of cooperative assemblies that follow a nucleation-elongation model[28]. Although the surprisingly high thermostability of 4sb-like assemblies ($T_m$=38-49° C.) over 36-mers reported previously ($T_m$=15-25° C.; FIG. 8a) could be attributable to the (POG)$_2$ extension, this addition is expected to increase the $T_m$ only by ~8° C.[29]. Thus, we believe that the additional interstrand salt bridges and uniform sticky-ends enabled by our design play a major role in improving assembly stability.

Figure 3B:
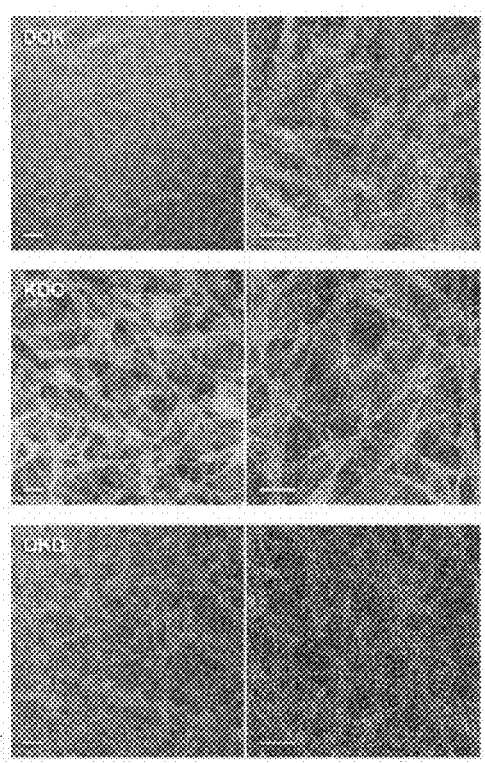
FIG. 3b depicts the TEM images of peptide assemblies. Scale bars: 30 nm.

Another outcome of our strategy is the absence of higher-order association of nanofibers, which we confirmed by negative-stained transmission electron microscopy (TEM) imaging. The 4sb-like fibers are <10 nm in diameter, are oriented and distributed irregularly, and exhibit features that are as fine as any synthetic collagen characterized previously (FIG. 3b). Interestingly, the trends among 4sb-like assemblies for thermostability and nanostructure overlap remarkably well (Table 1). DOK assemblies, which have the lowest thermostability (by CD) and smallest assembly size (by AUC), also form the widest nanofibers (mean±SD=8±2 nm). Comparison with previous TEM studies of single triple helices of natural collagen (~4 nm)[30,31] suggests that DOK fibers might be formed through the association of multiple triple helices. KDO and OKD nanofibers exhibit increasingly small diameters at 3.8±0.7 nm and 2.3±0.4 nm, respectively, consistent with a single triple helix. Whereas KDO and OKD both produce intertwined networks, KDO nanofibers have a greater tendency for bundling, commonly remaining aligned for 30-50 nm before separating.

Diameters were determined for OKD2 (2.0±0.4 nm) and OKD2-OKD2 (2.4±0.4 nm) using dry TEM samples. Characterization of the OKD2 and OKD2-OKD2 species is described in Table 2.

Figure 3C:
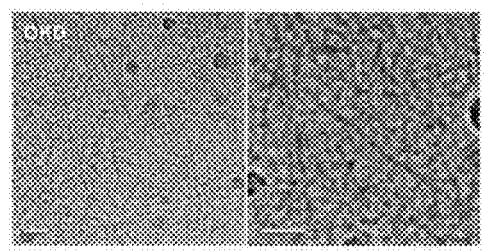
FIG. 3c depicts the vitreous ice cryo-TEM images of OKD nanofibers. Circular spots are ethane artifacts introduced during flash-freezing. Scale bars: 30 nm.
Figure 3D:
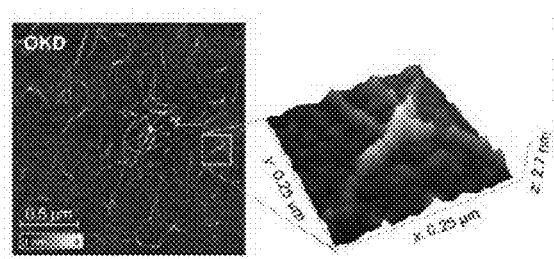
FIG. 3d depicts the OKD nanofibers imaged by AFM on freshly cleaved mica. Nanofibers retain their 1.2-nm diameter, even when overlaid.

The structure and stability of OKD nanofibers are most impressive. Although individual OKD nanofibers are not isolatable through dilutions, their bundling is rare, and triple-helical stretches can reach 0.3 μm in length. Properties of OKD assemblies remain largely the same when hydrated, as evidenced by cryo-TEM, a technique in which the solution structure is preserved by flash freezing in liquid ethane at −196° C. prior to imaging. Solvated nanofibers appear to be distributed randomly, and are intertwined extensively without forming bundles (FIG. 3c). These solvated nanofibers have a uniform diameter (3.8±0.5 nm) that is slightly thicker than those recorded for dried samples, likely due to tightly associated water and buffer molecules. Individual OKD nanofibers observed with tapping-mode atomic force microscopy (AFM) appear to be (1.2±0.2) nm thick and up to 0.5 μm long (FIG. 3d). Fiber diameter is maintained even when two fibers cross on the mica surface, as overlaid fibers are detected at twice the height of single fibers. Overall, data on OKD assemblies are indicative of nanofibers composed of a single triple-helix. Hence, the surprising stability of OKD assemblies must be due to interstrand rather than inter-helical interactions, providing the first demonstration of the strength attainable from sticky-ended CMP assembly.

TABLE 1

Assembly characteristics of 4sb-derived peptides.

| Peptide | $T_m$ (° C.) I = 20 mM | $T_m$ (° C.) I = 200 mM | Average oligomerization by AUC[a] | TEM imaging of assemblies Nanostructure and Bundling | Feature dimensions (nm) |
|---|---|---|---|---|---|
| OKD | 49 | 39 | >188 | single triple-helix (TH) nanofibers | 2.3 ± 0.4 |
| KDO | 46 | 38 | >61 | single-TH nanofibers intermittent bundling | 3.8 ± 0.7 |
| DOK | 38 | 31 | >47 | multiple-TH nanofibers no higher-level organization | 7.9 ± 2.2 |
| DOKctrl | 27 | 31 | 3[b] | none | — |

[a]Estimates for a lower-bound assembly size were obtained from a monomer + multimer model fit to AUC data at 15000 rpm, 4° C.
[b]OKDctrl data does not agree with a monomer + multimer model, fitting best to a trimer + multimer model dominated by the trimeric species. See FIG. 6

Figure 9:
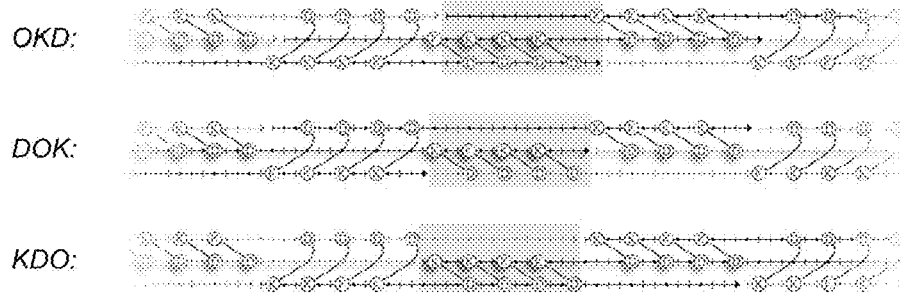
FIG. 9 depicts the uninterrupted triple helices in 4sb-like assemblies. OKD, DOK and KDO assemblies form near-identical uninterrupted triple-helical sections (highlighted in gray). All termini appear within a single XaaYaaGly-unit on the 4sb-template.

OKD, KDO, and DOK are designed to self-assemble by engaging in identical interactions specified by the 4sb-template and to generate nearly equivalent uninterrupted triple-helical segments (FIG. 9). Yet, the positioning of (PKG)$_4$- and (DOG)$_4$-blocks on the peptides influences both assembly stability and nanostructure. The low stability of DOK assemblies could be related to a lack of charge contacts between immediate neighbors in DOK assemblies (FIG. 10), which could destabilize sticky-ends in particular. A more general explanation becomes apparent upon consideration of triple-helical stability near CMP termini in an assembly. POG-repeats exhibit the highest triple-helical propensity, followed by DOG- and then PKG-repeats[32]. The thermostability of assemblies improves when sequences that better accommodate the collagen fold are placed near strand termini, keeping those termini associated closely with the growing nanofiber. In contrast, termini that associate loosely with the growing assembly could compromise structure (translating to larger diameters) and charge-pairing (translating to increased bundling). As CMP termini are displayed at the edges of the assembly as sticky-ends, improved triple-helical preorganization at the termini could also enhance assembly kinetics. Interestingly, these benefits require sequences of low triple-helical propensity to be central on the peptide. This behavior is dichotomous to that of blunt-ended triple helices, in which destabilization to central residues is most damaging to structure and stability[33].

Sequence Control Over Self-Assembly of Collagen Triple Helices.

Figure 5A:
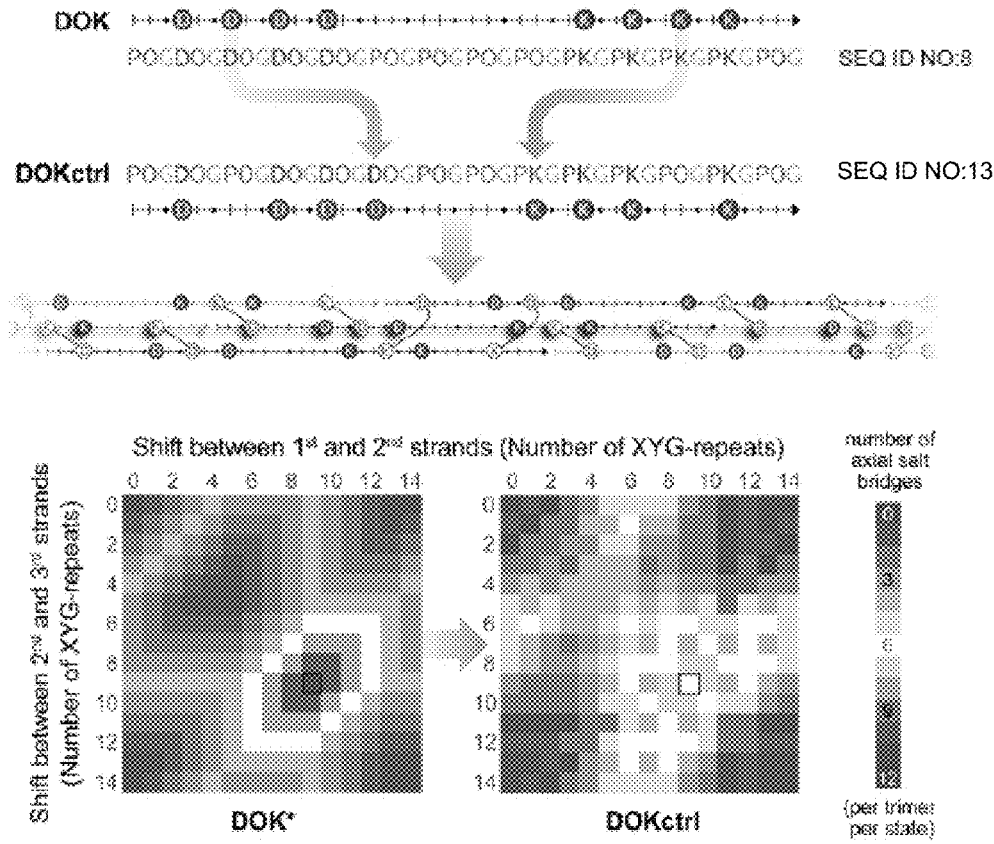
FIG. 5a depicts the representation of CMP sequences and strand-association landscapes for DOK and DOKctrl. Mutations to DOK destabilize its unique optimum for self-assembly and result in a landscape lacking any defining features. Symmetric association states for DOK and DOKctrl are marked with black borders. *This landscape describes strand-association for not only DOK, but all 4sb-derived peptides.
Figure 5B:
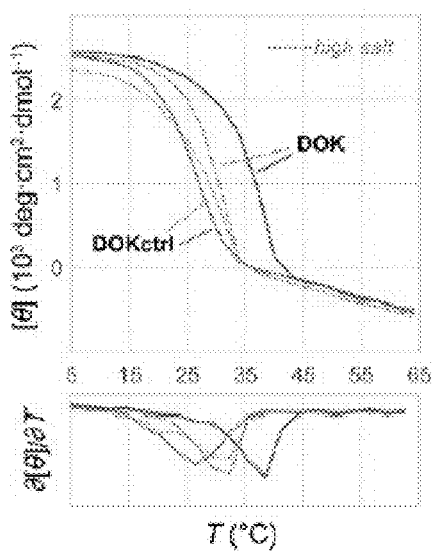
FIG. 5b depicts the CD thermal denaturation curves for DOK and DOKctrl determined at low ionic strength (20 mM; solid line) and high ionic strength (200 mM; dashed line), indicating diverging assembly pathways.
Figure 5C:
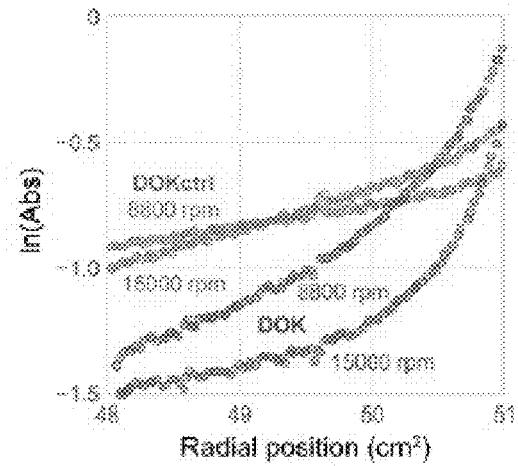
FIG. 5c, Equilibrium gradients during ultracentrifugation indicate different assembly regimes for DOK (steep gradients) and DOKctrl (shallow gradients).

Numerous sticky-ended association states can be generated for any CMP by varying the stagger between neighboring strands. The design of a CMP that leads to a sticky-ended assembly requires careful positioning of Lys and Asp residues on the sequence so that a minimal number of association states are stabilized maximally. FIG. 5a-c show that perturbing the strand-association landscape abolishes assembly.

Symmetric assembly enables perfect charge-pairing for a unique state on the strand-association landscape, and therefore, readily produces an exceptional design (FIG. 5a).

Altering the placement of Lys and Asp residues can disrupt the ideal landscape for CMP assembly. By swapping two pairs of residues on the DOK sequence (see 4sbG in Table 2), we created DOKctrl (see 4sbG-ctrl in Table 2), a CMP that maintains the sequence composition and charge distribution of DOK but has a featureless strand-association landscape (FIG. 5a). Interestingly, this minor sequence modification is expected to diminish only the prospect for sticky-end formation, but not blunt-ended assembly. The stark difference observed between DOK and DOKctrl structures provide experimental confirmation for the sticky-ended assembly of DOK. Whereas DOKctrl ($T_m=27°$ C.) forms a less stable assembly than does DOK ($38°$ C.) at low ionic-strength (I=20 mM), increasing ionic strength to 200 mM with NaCl removes this difference ($T_m=31°$ C. for both DOK and DOKctrl) (FIG. 5b). Divergent responses to weakening Coulombic interactions suggest disparate modes of association. AUC provides further support for this idea by revealing two distinct association regimes for DOK (>47-mer) and DOKctrl (trimers) (FIG. 5c and FIG. 6). In addition to providing evidence for sticky-ended assembly, the design of nearly identical CMPs that are productive (DOK) and unproductive (DOKctrl) for assembly also demonstrates the tight control that sequence exerts over nanostructure, a new concept for collagen-based nanomaterials.

Experimental Procedures

Peptide Synthesis

All CMPs were synthesized on polyethylene glycol-based resins on a Prelude peptide synthesizer from Protein Technologies (Tucson, Ariz.) using standard Fmoc-based methods at the Peptide Synthesis Facility of University of Wisconsin-Madison (UW) Biotechnology Center (biotech.wisc.edu/services/peptidesynth). Condensation of Fmoc-ProHypGly-OH[14] or Fmoc-GlyProHyp-OH tripeptide segments from Bachem (Bubendorf, Switzerland) was employed wherever applicable. Fmoc removal was achieved in piperidine (20% v/v in DMF), and peptide building blocks (4 equiv), activated through treatment with HATU and NMM, were coupled to the free amine of the growing chain for 60 min. Addition onto Pro or Hyp residues were performed through 30-min double couplings. Peptides were cleaved from the resin and deprotected in 95:2.5:2.5 TFA/triisopropylsilane/water (1.5-2.0 mL), precipitated from methyl t-butyl ether below 0° C., and isolated by centrifugation.

Figure 12:
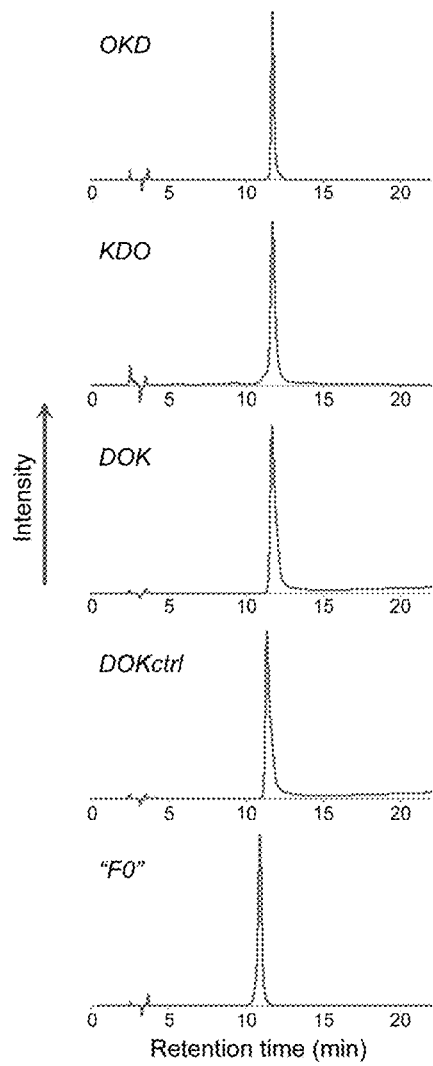
FIG. 12 depicts the HPLC chromatograms of purified CMPs (reverse-phase analytical HPLC chromatograms of peptides synthesized and purified for this study.)
Figure 13A:
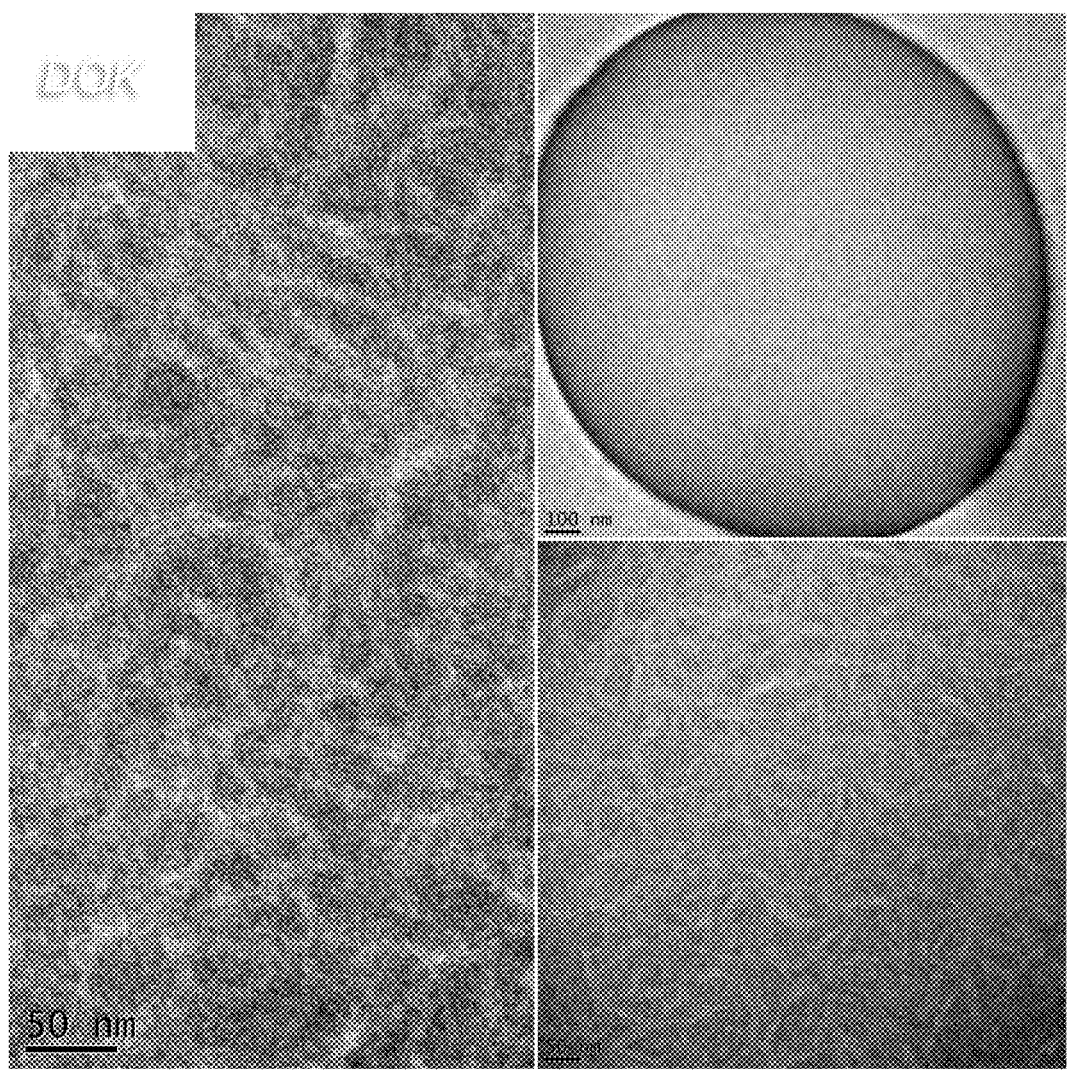
FIG. 13a depicts TEM images of dried DOK samples.
Figure 13B:
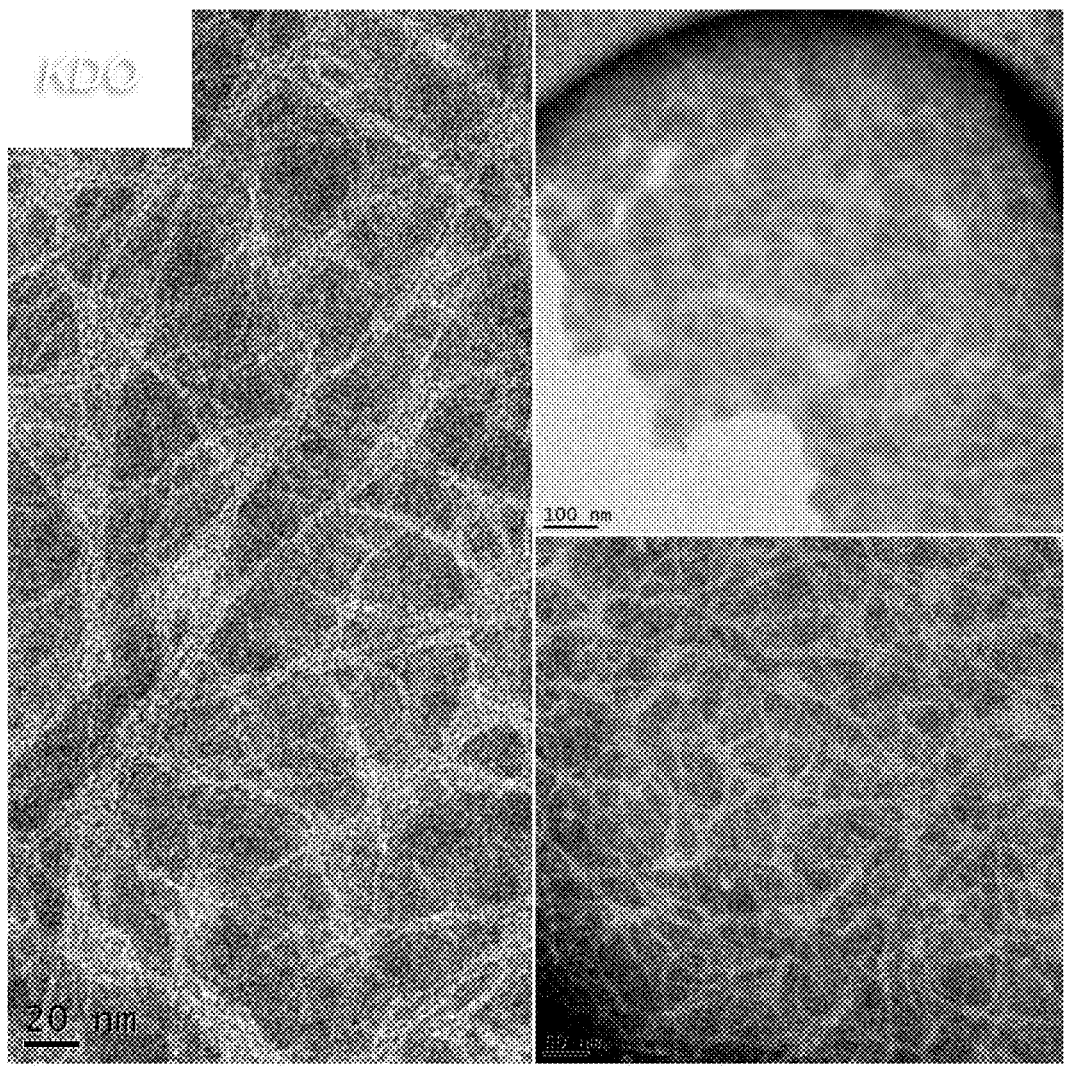
FIG. 13b depicts TEM images of dried KDO samples.
Figure 13C:
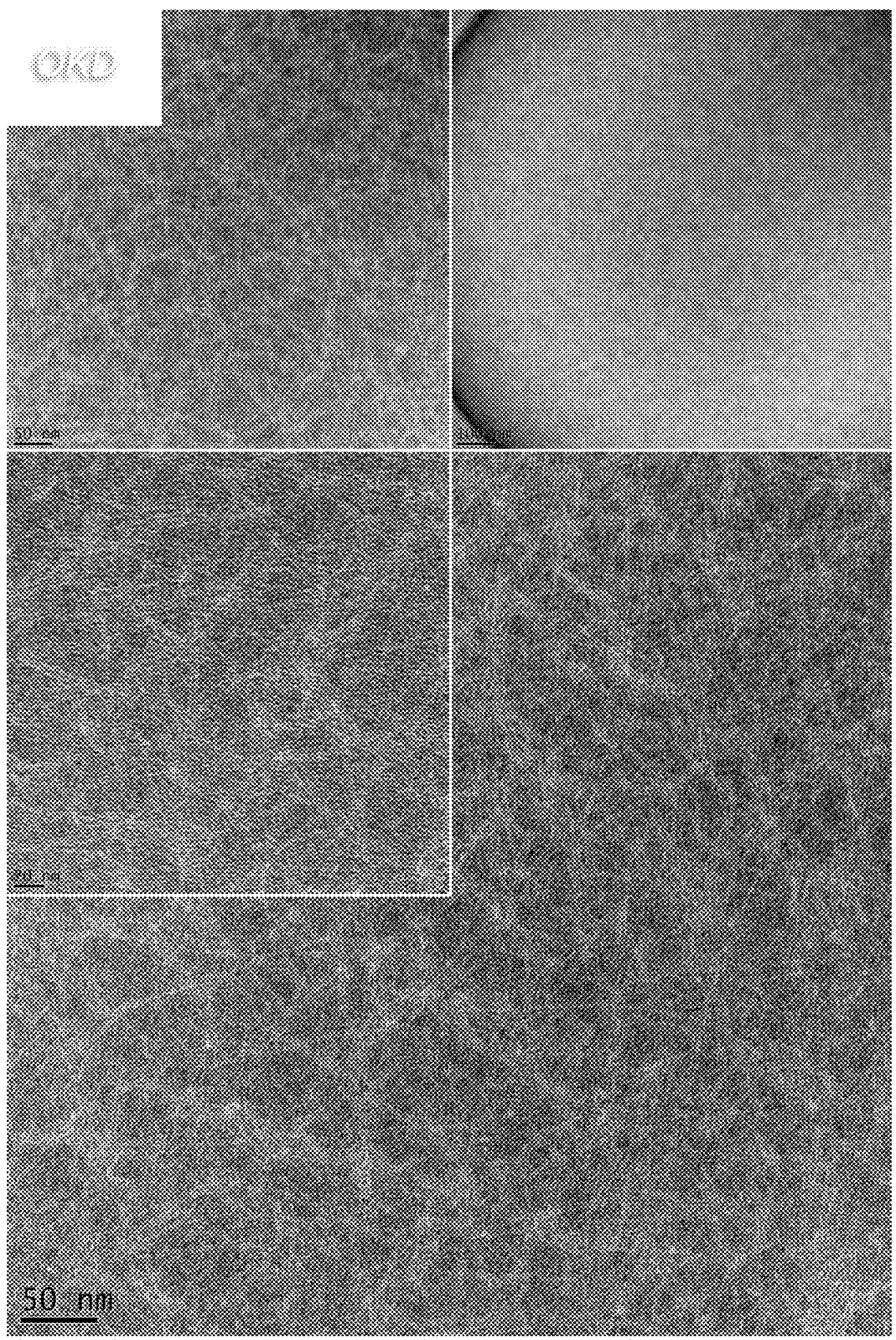
FIG. 13c depicts TEM images of dried OKD samples.
Figure 13D:
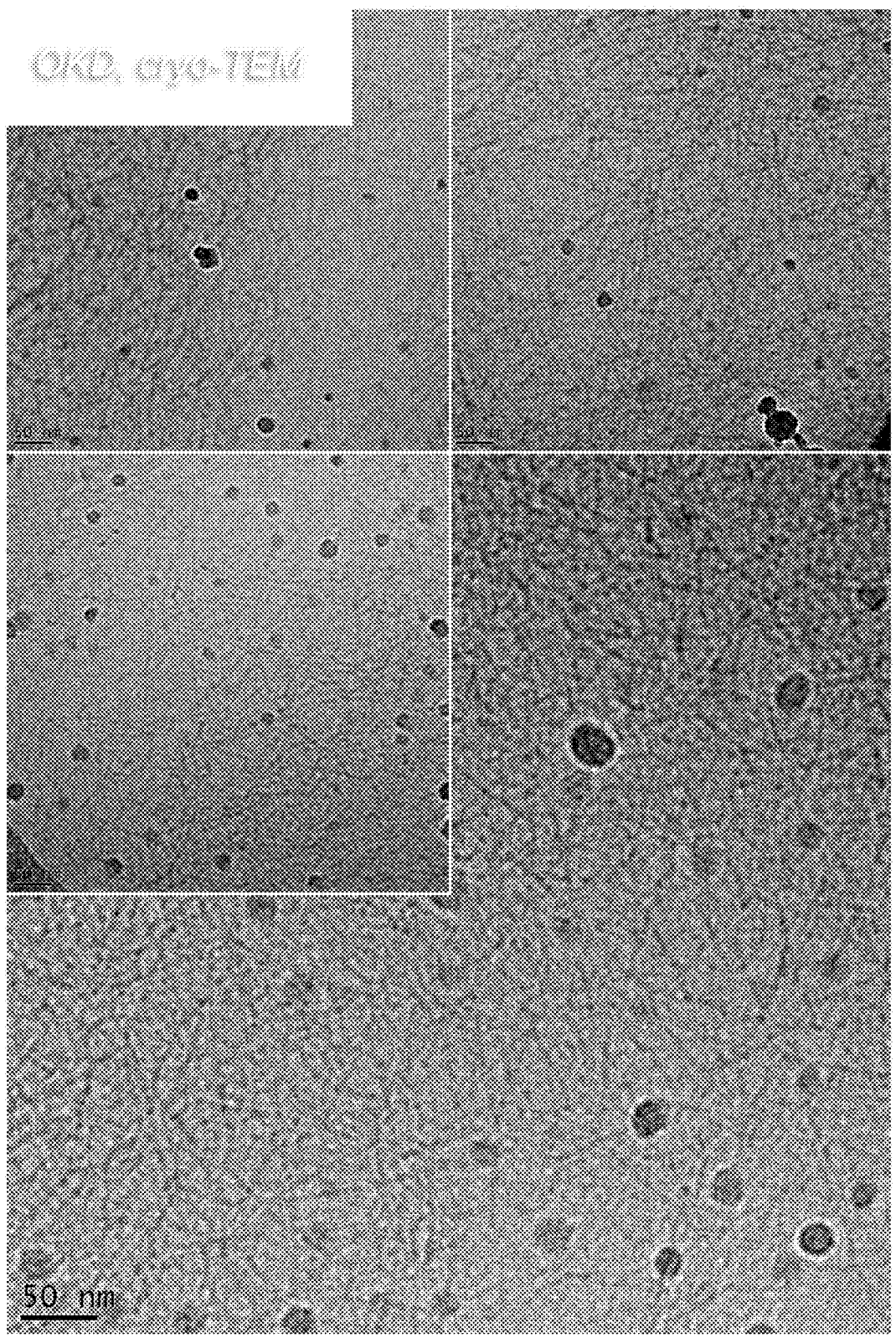
FIG. 13d depicts cryo-TEM images of OKD assemblies.

Dried crude peptides were dissolved in 0.1% v/v TFA and filtered and purified by preparative HPLC at 45° C. using gradients of CH3CN/water containing 0.1% v/v TFA on a Shimadzu Prominence instrument from Shimadzu (Kyoto, Japan) equipped with a VarioPrep 250/21 C18 column from Macherey-Nagel (Duren, Germany). All peptides were >90% pure according to analysis with analytical HPLC and MALDI-TOF mass spectrometry (MS). MALDI-TOF analysis was carried out with a Voyager DE-Pro mass spectrometer from Thermo Fischer Scientific (Waltham, Mass.) at the UW Biophysics Instrumentation Facility (BIF; biochem.wisc.edu/bif). For all 42-residue peptides, (m/z) [M+H]$^+$ calcd 3889.8, found 3889.5 for OKD; found 3890.0 for KDO; found 3889.3 for DOK; found 3890.1 for DOKctrl. For F0[19], calcd 3355.6, found 3355.4. Analytical HPLC chromatograms for purified peptides are displayed in FIG. 12.

Circular Dichroism Spectroscopy

All CD data were acquired with a 202SF or 420 CD spectrophotometer from Aviv Biomedical (Lakewood, N.J.) at the UW BIF. Samples were prepared at a concentration of 0.6 mg/mL (~160 μM) in 10 mM sodium phosphate buffer, pH 7.0, both with and without NaCl (180 mM). CD spectra were recorded at 4° C. with a 1-nm band-pass in quartz cuvettes with a 0.1-cm pathlength, using an averaging time of 4 s. For thermal denaturation experiments the CD signal was monitored at 226 nm while the sample was heated at a rate of 12° C./h in 2- or 3-° C. steps. The melting transition is indicated by a minimum on the temperature derivative of the melting curve ($\partial[\theta]/\partial T$), and values ($\pm 1°$ C.) of melting temperature ($T_m$) were determined assuming constant curvature in the immediate vicinity of the transition minimum.

Thermal denaturation experiments were performed in a high ionic strength condition (10 mM sodium phosphate buffer, pH 7.0, containing 180 mM NaCl; I=200 mM) and a low ionic strength condition (10 mM sodium phosphate buffer, pH 7.0; I=20 mM), and the results of these experiments are presented in FIGS. 5b (DOK and DOKctrl) and 8b (OKD and KDO). CMP assemblies that are not prone to homotrimer formation experience a 7-10° C. drop in $T_m$ upon an order-of-magnitude increase in ionic strength, consistent with electrostatic stabilization of assemblies.

Among self-assembling 36-mer CMPs designed by Hartgerink and coworkers, the F0 peptide[19] exhibits higher thermostability ($T_m=40°$ C.) than do others ($T_m=15\text{-}25°$ C. for A1, A2, F1 and F2)[21]. To explore whether this surprising thermostability is due to sticky-ended triple-helix formation or to higher-order assembly, we monitored F0 denaturation at different concentrations by CD spectroscopy (FIG. 8a). At low concentration, the F0 assemblies display a single melting-transition near 25° C., while increasing F0 concentration promotes a second transition near 40° C. Both F0 phases co-exist at 0.6 mg/mL, the room-temperature transition being prominent, while at 1.8 mg/mL the 40° C. transition dominates. We do not believe the two transitions correspond to different structures at the strand-association level, as the appearance of the 40° C. transition does not lead to a drastic change in CD signal. A more likely explanation is the concentration-dependent formation of higher-order F0 assemblies, which could boost the thermostability without inducing a significant change in triple-helical content. Thus, we believe a ~25° C. melting temperature better reflects the thermostability of sticky-ended F0 assemblies.

Analytical Ultracentrifugation

Sedimentation equilibrium experiments were performed at the UW BIF with an XL-A analytical ultracentrifuge from Beckman Coulter (Brea, Calif.) equipped with an An-60 Ti rotor. Samples were prepared at 0.6 mg/mL in 10 mM sodium phosphate buffer, pH 7.0, but were diluted to 0.3 mg/mL prior to the experiment. Sample (100 μL) and matching buffer (110 μL) were placed in a cell with an Epon 12-mm double-sector charcoal-filled centerpiece from Beckman Coulter. Experiments were run at 4° C. for more than 7 days at speeds of 8.8, 15, 25, 36, and 60 k rpm, and gradients recorded at 231 nm were monitored until superimposable 4 h apart. A buffer density of 1.0011 g/mL and a partial specific volume of 0.6955 mL/g calculated based on amino-acid content was used for analysis. Equilibrium gradients at 4° C. were modeled as single and multiple non-interacting species through nonlinear least-squares fits to gradient data. Analysis was performed with programs written for IGOR PRO software from WaveMetrics (Lake Oswego, Oreg.) by Dr. D. R. McCaslin (UW BIF). Non-sedimenting baselines between 0.04-0.07 OD were applied for all samples during analysis. Plots of gradients at 15 k rpm and their fits to multiple-species models are shown in FIG. 6.

Assembly of OKD, KDO, and DOK into large structures was apparent, as the shift of mass from meniscus to cell bottom was observed even at the start-up speed of 3 k rpm. Peptides in this work were not designed to assemble into structures of a specific size, and hence equilibrium gradients were expected to feature many different species with a wide range of molecular weights (MWs), requiring complex models featuring numerous interacting species for an accurate description. The two-species models we employ consist of a low- and a high-MW species, which is a gross simplification of the self-assembly process. Nevertheless, these models describe the gradients at a reasonable level, especially when monomers are included as the low-MW species. The high-MW species represents the behavior of a complex peptide oligomer mixture. A higher mass is assigned to this species when steeper equilibrium gradients are modeled. This value constitutes a lower-bound for the weight-average oligomer size, since the amount of depleted material at the cell bottom cannot be determined accurately. This value is highly sensitive to acquisition-speed and fit parameters, yet the trends revealed between different peptides are not sensitive to such factors. We list the oligomerization state of the high-MW species assigned at 15 k rpm to highlight differences in the extent of assembly between OKD, KDO and DOK (Table 1).

DOKctrl gradients are dominated by a trimer at low speeds, but the gradients cannot be explained by a trimer alone. Application of a two-species trimer+multimer model to low-speed data (8.8 and 15 k rpm) makes use of a 54-mer component to describe large masses at the cell bottom. In contrast to those of DOK and KDO, DOKctrl gradients harbor small amounts of this high-MW species (FIG. 6). Correspondingly, DOKctrl exhibits minimal depletion when compared with peptides designed for self-assembly. Although the mechanism is not apparent, we suspect concentration-induced blunt-ended assembly (FIG. 1b) for the presence of such high-MW components. The absence of multiple DOKctrl phases in the thermal denaturation experiments, and their improved thermostability at high ionic strength supports this idea.

Transmission Electron Microscopy

All imaging was performed with a Tecnai TF-30 TEM instrument (300 kV) from FEI (Hillsboro, Oreg.) at the UW Materials Science Center (MSC; msc.engr.wisc.edu). Samples were prepared on Quantifoil R1.2/1.3 holey-carbon mesh on copper grids. Sample preparation for dry TEM was carried out at 4° C. Samples were negative-stained using freshly prepared 2.0% w/w PTA solution adjusted to pH 6 with aqueous NaOH and filtered. The peptide solution was allowed to adhere to the carbon-mesh side of the grid for 1 min, at which point excess solution was blotted with filter paper, and the grid was allowed to dry for 5 min. Negative stain was applied for 10 min by inverting the grid on a drop of PTA solution. Excess stain was removed with filter paper, and the grid was allowed to dry overnight prior to imaging. For vitreous ice cryo-TEM imaging, a solution of OKD (0.3 mg/mL) was applied to a TEM grid, glow discharged for 0.5 min at 25 mA beforehand with a Pelco easiGlow unit from Ted Pella (Redding, Calif.). The grid was allowed to equilibrate at 5° C. at 95% humidity. A drop of peptide solution was added, and the grid was then blotted and immersed in liquid ethane on a Vitrobot from FEI. The grid was transferred from liquid ethane to liquid nitrogen manually, and was stored in liquid nitrogen until imaging. Acquisition was performed at −180° C. with low dose and long exposures. Additional TEM and cryo-TEM images collected on DOK, KDO, and OKD nanofibers are presented in FIG. 13.

Atomic Force Microscopy

Peptide samples were annealed at 0.03 mg/mL in 10 mM sodium phosphate buffer, pH 7.0, and applied onto freshly cleaved mica at 4° C. After 10 min, the solution of peptide was washed with cold water for 30 s, and excess water was removed with a filter paper. Samples were dried at 4° C. overnight prior to imaging. AFM images were collected in tapping mode with an Agilent 5500 SPM instrument using NCHV-A probes from Bruker (Billerica, Mass.). Data were analyzed with Gwyddion ver. 2.39 software (gwyddion.net).

Figure 14:
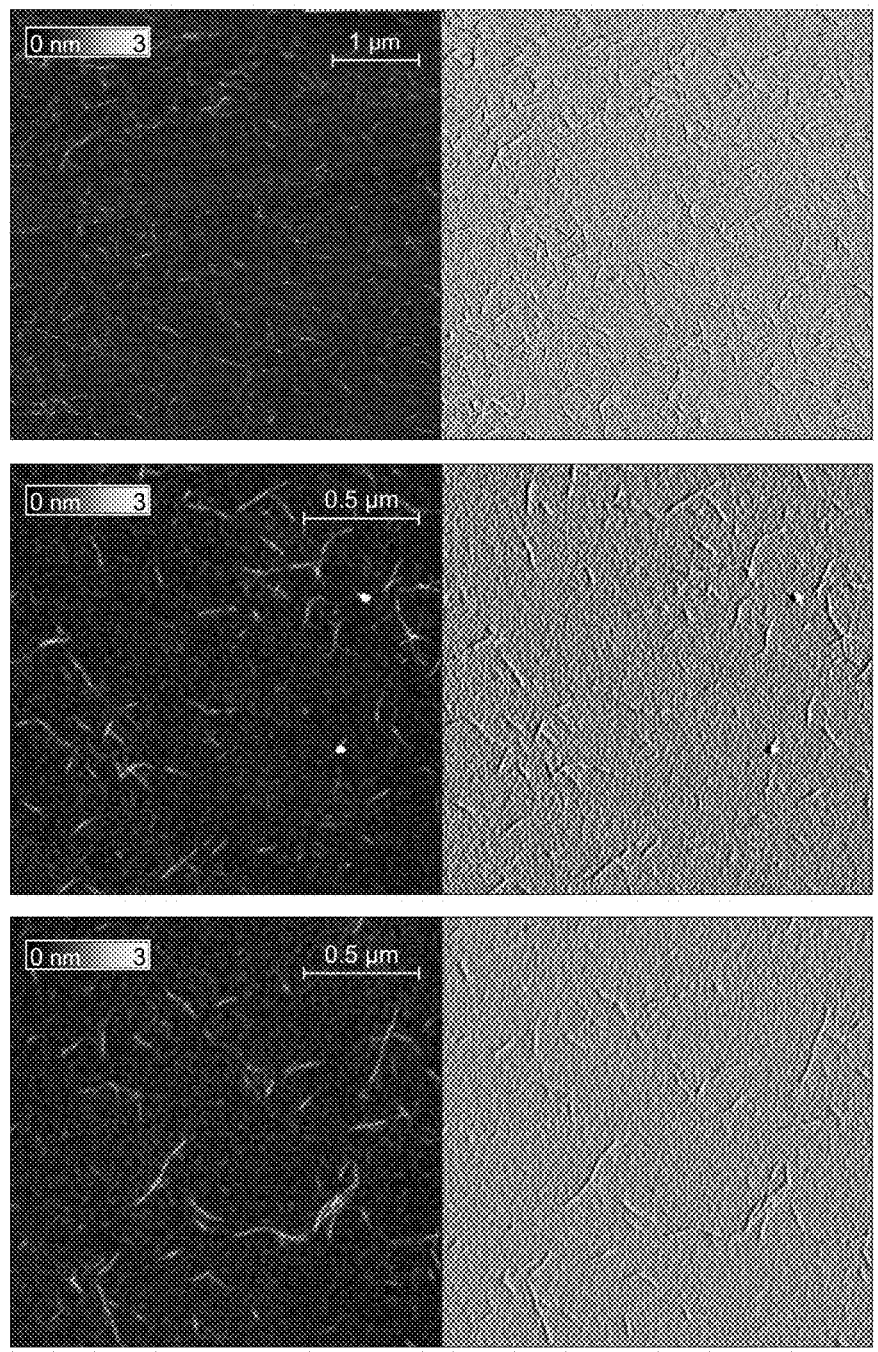
FIG. 14 depicts additional AFM images of OKD assemblies. Probe amplitude data (right) is shown to facilitate identification of features in the height images (left).

Additional AFM images collected on OKD nanofibers are provided in FIG. 14. Although the softness of the material led to artifacts and necessitated frequent use of fresh probes, the images clearly and consistently present the self-assembled OKD nanofibers.

Strand-Association Landscapes

Construction

Association states for sticky ended assemblies were enumerated through a set of purpose-written scripts in Python (v.2.7) that construct all possible offsets between three infinite, periodic strands given a CMP sequence. An input sequence of the form $(XaaYaaGly)_n$ is repeated without gaps to create a periodic, infinite strand, which is paired with two other identical strands to create an infinite homotrimer. The strands of the infinite homotrimer are shifted with respect to each other to produce all possible strand-association states. For each state, any instances of Lys•••Asp pairs positioned to enable an axial contact are identified, and their counts are reported on the strand-association landscape (FIG. 5a).

An infinite homotrimer approximation overlooks the impact of peptide termini placement, but captures all side-chain-side-chain interactions for any CMP that follows the sticky-ended assembly route. In this way, the strand-association landscape provides a comprehensive overview of all sticky-ended associations, and allows identification of productive and/or competing states. The infinite-strand approximation also ensures that circular permutations to the CMP sequence do not alter the strand-association landscape. Thus, all peptides constructed based on the 4sb-template (FIG. 1f) share the same strand-association states and landscapes (FIGS. 5a and 7a), irrespective of the 42-residue section under consideration.

The number of XaaYaaGly-shifts that offset any two strands of a sticky-ended trimer is determined relative to a reference state with zero offset. In this work, this offset is defined to be zero when two strands have a single-residue stagger, and the $i^{th}$ and $i^{th}+1$ strands are leading and lagging, respectively, ensuring that the coordinate [0, 0] on the strand-association landscape refers to the "blunt-ended" association state.

Properties

Strand-association states (SASs) are uniquely defined by the number of XaaYaaGly-offsets between any two pairs of strands. In this work, we have used offsets between the $1^{st}$ and $2^{nd}$, and $2^{nd}$ and $3^{rd}$ strands for this purpose. The assignment of the $1^{st}$ strand is arbitrary for an infinite homotrimer. Once assigned, the $1^{st}$ strand is set as the "leading strand", allowing the assignment of "middle" and "lagging" strands as $2^{nd}$ and $3^{rd}$. For strands i and j, $\Delta(i-j)$ represents the XaaYaaGly-offset between $i^{th}$ and $j^{th}$ strands.

Figure 15A:
FIG. 15a depicts a 0.5% OKD2 hydrogel disk photographed next to the 8-mm parallel-plate rheometer stage.
Figure 15B:
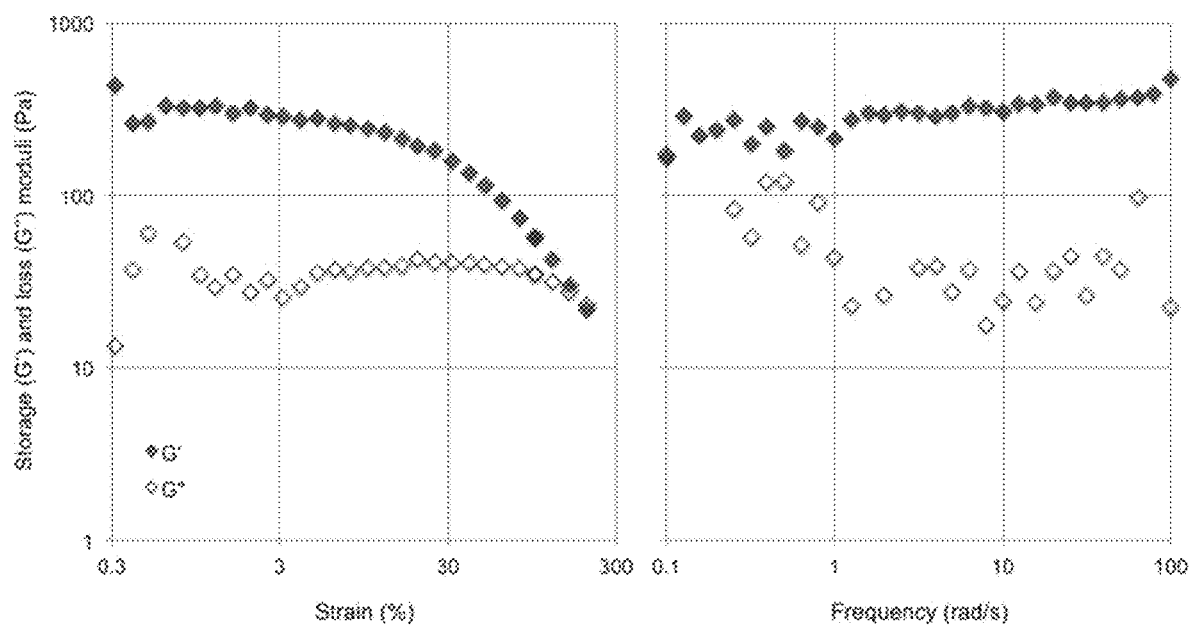
FIG. 15b depicts strain and frequency sweeps on a 0.5% OKD2 hydrogel in 10 mM phosphate buffer (pH=7) obtained at room temperature.

The strand-association landscape presents the number of axial contacts for each SAS (FIG. 5a; FIG. 15b), comprehensively describing all possible states for a given sequence cataloged by $\Delta(1-2)$ and $\Delta(2-3)$ offsets.

Since the assignment of the "$1^{st}$ strand" is arbitrary, most SASs are represented three times on this landscape, at coordinates [$\Delta(1-2)$, $\Delta(2-3)$], [$\Delta(2-3)$, $\Delta(3-1)$], and [$\Delta(3-1)$, $\Delta(1-2)$]. The symmetric association state is the only exception to this rule. Symmetric association ensures that all strand offsets are identical (i.e., $\Delta(1-2)=\Delta(2-3)=\Delta(3-1)$), and is the only state to appear once on the strand-association landscape. Consequently, the number of non-redundant strand-association states ($n_{SAS}$) for a single-CMP assembly system is $n_{SAS}=\lceil n_T^2/3 \rceil$
where $n_T$ is the number of XaaYaaGly-trimers in the CMP sequence, and the ceiling function ($\lceil\ \rceil$) accounts for the symmetric association state when present.

By definition, states that neighbor each other vertically or horizontally on the strand-association landscape are separated by a single-XaaYaaGly shift between their strands. Horizontal movements are equivalent to moving the $1^{st}$ strand with respect to the $2^{nd}$, and vertical movements are equivalent to moving the $3^{rd}$ strand with respect to the $2^{nd}$. In addition, movements in the direction of the bottom-left-top-right diagonal are equivalent to shifting the $2^{nd}$ strand with respect to the $1^{st}$ and $3^{rd}$, and also constitute single-XaaYaaGly shifts. An example of this shifting can be seen on the "DOK" panel in FIG. 5a, where a single-XaaYaaGly shift away from the symmetric association state by any strand reduces the number of possible axial interactions from 12 to 10.

Heterotrimeric Infinite Strands

Strand-association landscapes can also be constructed for sticky-ended assemblies wherein peptides of different composition occupy different strands. Such cases require the construction of AAB- or ABC-type infinite heterotrimers. With distinct sequences on each strand, explicit assignment of strand numbers becomes necessary. As a result, the coordinates [$\Delta(1-2)$, $\Delta(2-3)$], [$\Delta(2-3)$, $\Delta(3-1)$], and [$\Delta(3-1)$, $\Delta(1-2)$], redundant for an infinite homotrimer, point to distinct association states in a heterotrimeric system.

For ABC-type heterotrimers, two different strand orders (ABC and ACB) are possible. For such systems, different strand-association landscapes are necessary for each strand ordering, as a single coordinate, [$\Delta(1-2)$, $\Delta(2-3)$], cannot represent both [$\Delta(A-B)$, $\Delta(B-C)$] and [$\Delta(A-C)$, $\Delta(C-B)$] on a single landscape. Hence, a single homotrimeric SAS with redundancies evolves into 6 distinct states on an infinite ABC heterotrimer, analogous to 6 registers being available to a blunt-ended heterotrimer A set of strand offsets (i.e., $\Delta(i-j)$ for all strand pairs) for a sticky-ended heterotrimer with known strand ordering produces three distinct SASs for both AAB- and ABC-type heterotrimers. This relationship is true for all SASs but the symmetric association state, where this information uniquely specifies a single SAS. This property could provide an additional advantage for symmetrically designed CMPs, as the field moves on to more complex, multi-component or multi-stranded assembly systems.

Discussion

There are 66 unique strand-association states available to 4sb-like peptides (FIG. 7a). Examination of these states reveals that diminishing triple-helical overlap between three strands is always balanced with additional axial salt bridges as the trimer advances from a blunt-ended to a sticky-ended configuration. This balance is not accessible for F2, a similarly constructed CMP that does not support symmetric assembly[21]. The accepted association state for F2 (FIG. 1c) supports the longest uninterrupted triple-helix among five top-performing states, yet its short overhangs bear no opportunity for additional axial contacts through further self-assembly. Therefore, assembly through this state requires the formation of sticky-ended homotrimers a priori, consistent with a hierarchical-assembly mode[19,21] (FIG. 7b). In contrast, symmetric assemblies extend uniformly and free of "weak" regions, allowing CMP building blocks to add directly to the fiber. Moreover, because the symmetric-association state is unique, its stabilization does not lead to unintended competing states with matching performance (FIG. 11). Hence, the symmetric assembly algorithm both simplifies the design process and increases its likelihood of success.

Symmetric assembly is possible for all CMPs of size $n_T=3v\pm1$ through a unique strand-association state, which can be stabilized through axial salt bridges or other means. In this work, we have applied these principles to a self-assembling single-peptide system. Symmetry would, however, benefit any system in which peptide building blocks appear on every strand of the assembled triple-helix. Indeed, the patterns set by peptide tessellations provide a blueprint for the design and construction of currently inaccessible self-assembling systems that involve multiple CMPs. Co-assembling CMPs could be designed on a symmetric-assembly template so that, though peptides violate the template individually, the template would be reinstated upon co-assembly (FIG. 7c). Such units could also be stapled together to generate complex building blocks[26]. The benefits of symmetry can transfer to other systems that are based on a symmetric template, just as shapes created by merging adjacent pairs of tessellating tiles with p1 symmetry (or dividing such tiles) also tessellate (FIG. 1d and FIG. 4). Further, the design of multiple self-assembling peptides built on incompatible templates (e.g., an xy- and a yx-template) could produce sets of CMPs that assemble independently, even when mixed. In theory, elements that allow programmed triple-helical association[34,35] can also be encoded into CMPs. Our current work enables the production of "human-scale" triple-helices. An expanded CMP toolkit would enable the control of size, strength, and orientation of synthetic collagen fibrils that mimic connective tissues (such as skin and cartilage) in which multiple types of fibrillar collagens interact[36].

Conclusions

Despite its ancient origin, paramount importance in modern biology, and repetitious architecture[12], the collagen triple-helix has been a challenging target for controlled self-assembly. The symmetric assembly rules that we present arise from fundamental aspects of collagen structure and allow easy access to sticky-ended fibrillation. Nanofibers enabled by symmetric design owe their extraordinary stability solely to the sticky-ended association of peptides, and yield extended human-scale triple-helices. Although the self-assembly "alphabet" available for CMP-based nanostructures is crude in comparison with DNA/RNA, the ease of their interfacing with both biology[9] and nanotechnology[16,37] encourage their development.

Example 2

Table 2 provides a list of peptides that work in the practice of this invention. These peptides follow the following criteria for symmetric triple-helical self-assembly:

o. Peptides should embody the uninterrupted Xaa-Yaa-Gly tripeptide repeats of collagens Peptides should be constructed to allow the formation of a polyproline-II helix. For this, their sequence should have a Gly at every third position. In addition, Pro residues should be favored at Xaa positions and Pro or Hyp residues at Yaa positions. Resulting peptides are collagen-mimetic peptides (CMPs).

i. Repulsive interstrand interactions should be installed to prevent the formation of the blunt-ended homotrimeric state.

CMPs are prone to forming blunt-ended triple helices, in general. This state should be destabilized to enable CMPs to associate with sticky-ends.

ii. The number of tripeptide repeats, $n_T$, that constitute the CMP cannot be evenly divisible by three.

Satisfaction of this criterion is essential to obtain identical strand-offsets in the assembled state. Triple-helical structure does not allow peptides with counts of tripeptide repeats ($n_T$) evenly divisible by three ($n_T$ 3v, where v is a positive integer) to associate through uniform strand offsets.

iii. Interstrand interactions should be designed to support sticky-ended association with $n_T$-residue overhangs for a peptide with $n_T$ tripeptide repeats.

An assembly without "weak sections" requires the offset that separates any neighboring CMPs to be identical. This offset is $n_T$ residues for a peptide with $n_T$ tripeptide repeats. Although restriction of peptide size to $n_T$=3v±1 tripeptide repeats ensures the accessibility of uniform, $n_T$-residue sticky-ends, it does not guarantee it. Thus, it is necessary to introduce attractive interstrand interactions to CMP designs that stabilize triple-helix formation only when they associate with $n_T$-residue offsets.

Table 3 provides a list of peptides that do not form discernible fibrillar assemblies, and the assembly rules that are violated are indicated. Peptides that utilize ornithine (Or) in place of Lys experience a significant destabilization of their potential interstrand salt bridges, which usually prevents them forming detectable fibers. Other sequences use Lys and Asp salt bridges, but their placement on the sequence does not adequately support symmetric association. In both situations assembly rule iii is violated.

TABLE 2

Peptide constructs that self-assemble into symmetric extended triple helices. Interstrand disulfide bridges between Hcy and Cys residues on different strands are indicated by the alignment of the participating residues in the sequence.

| Name/Sequence | SEQ ID NO | $n_T$ | Evidence | $T_m$ (° C.) |
|---|---|---|---|---|
| 3sb-KDO<br>PKGPKGPKGP<br>OGPOGDOGDOG<br>DOGPOGPOGPO | 19 | 11 | assembly (AUC/CD/DLS) | 13 |
| 3sb-OKD<br>POGPOGPOG<br>PKGPKGPKGP<br>OGPOGDOGDO<br>GDO | 21 | 11 | large assemblies or aggregation (AUC/CD) | 20 |
| 3sbG-KDO<br>PKGPKGPKGP<br>OGPOGDOGDO<br>GDOGPOGPOG<br>POG | 22 | 11 | assembly (AUC/CD) | 26 |
| 4sb<br>POGDOGDOG<br>DOGDOGPOGP<br>OGPOGPOGPK<br>GPKGPKGPKG<br>PO | 23 | 14 | fibrillar assembly (AUC/CD/AFM/TEM) | 29 |
| 4sb-KDO<br>PKGPKGPKGP<br>KGPOGPOGDO<br>GDOGDOGDOG<br>POGPOGPOGP<br>O | 24 | 14 | fibrillar assembly (AUC/CD/AFM/TEM) | 33 |
| 4sb-OKD<br>POGPOGPOGPO<br>GPKGPKGPKGP<br>KGPOGPOGDOG<br>DOGDOGDO | 26 | 14 | fibrillar assembly (AUC/CD/AFM/TEM) | 36 |
| 4sbG ("DOK")<br>POGDOGDOGDO<br>GDOGPOGPOGP<br>OGPOGPKGPKG<br>PKGPKGPOG | 8 | 14 | fibrillar assembly (AUC/CDTEM) | 38 |
| 4sbG-KDO ("KDO")<br>PKGPKGPKGPK<br>GPOGPOGDOGD<br>OGDOGDOGPOG<br>POGPOGPOG | 9 | 14 | fibrillar assembly (AUC/CD/TEM/DLS) | 46 |
| 4sbG-OKD ("OKD")<br>POGPOGPOGPO<br>GPKGPKGPKGP<br>KGPOGPOGDOG<br>DOGDOGDOG | 2 | 14 | fibrillar assembly, hydrogel (AUC/CD/TEM/AFM/DLS/Rheology) | 49 |
| 3sbG-OKD<br>POGPOGPOGPK<br>GPKGPKGPOGP<br>OGDOGDOGDOG | 27 | 11 | fibrillar assembly (CD/TEM) | 33 |
| 4sbG-OKD2<br>POGPOGPOGPK<br>GPKGPKGPKGPO<br>GPOGDOGDOGDO<br>GDOGPOG | 28 | 14 | fibrillar assembly, hydrogel (CDTEM/DLS/Rheology) | 50 |
| 8hc8<br>POGPOGPOGP<br>OGPOGHcyOGP<br>OGPOG<br>(SEQ ID NO: 36)<br>POGPOGPCysGPO<br>GPOGPOGPOG<br>(SEQ ID NO: 37) | 29, 30 | 8-8 | assembly (CD/AUC/DLS) | 37 |

TABLE 2-continued

Peptide constructs that self-assemble into symmetric extended triple helices. Interstrand disulfide bridges between Hcy and Cys residues on different strands are indicated by the alignment of the participating residues in the sequence.

| Name/Sequence | SEQ ID NO | $n_T$ | Evidence | $T_m$ (° C.) |
|---|---|---|---|---|
| OKD2-OKD2<br>POGPOGPOGPKG<br>PKGPKGPKGHcy<br>OGPOGDOGDOGD<br>OGDOGPOG<br>(SEQ ID NO: 38)<br>POGPOGPCysGP<br>KGPKGPKGPKGP<br>OGPOGDOGDOGD<br>OGDOGPOG<br>(SEQ ID NO: 39) | 31, 32 | 14-14 | fibrillar assembly (CDTEM/DLS) | 60 |
| OKO2-OOD2<br>POGPOGPOGP<br>KGPKGPKGPKG<br>HcyOGPOGPOG<br>POGPOGPOGPO<br>G<br>(SEQ ID NO: 40)<br>POGPOGPCysG<br>POGPOGPOGPO<br>GPOGPOGDOGD<br>OGDOGDOGPOG<br>(SEQ ID NO: 41) | 33, 34 | 14-14 | fibrillar assembly (CD/TEM/DLS) | 57 |
| 4sbG-OKDO<br>POGPOGPKGPKG<br>PKGPKGPOGPOG<br>DOGDOGDOGDOG<br>POGPOG | 35 | 14 | fibrillar assembly, hydrogel (CD/TEM/DLS/Rheology) | 47 |
| 4sbG-KDO2<br>POGPKGPKGPKG<br>PKGPOGPOGDOG<br>DOGDOGDOGPOG<br>POGPOG | 36 | 14 | fibrillar assembly (CD/TEM/DLS) | 42 |
| 4sbG-gap4<br>POGPOGPOGPKG<br>PKGPKGPKGPKG<br>POGDOGDOGDOG<br>POGDOG | 37 | 14 | assembly, hydrogel (CD/DLS/Rheology) | 50 |
| OKD2-C8<br>POGPOGPCysGP<br>KGPKGPKGPKGP<br>OGPOGDOGDOGD<br>OGDOGPOG | 32 | 14 | assembly (CD/DLS) | 45 |
| OKD2-h22<br>POGPOGPOGPKG<br>PKGPKGPKGHcy<br>OGPOGDOGDOGD<br>OGDOGPOG | 31 | 14 | assembly (CD/DLS) | 50 |

TABLE 3

Peptide constructs tested that do not reliably self-assemble.

| Name/Sequence | SEQ ID NO | $n_T$ | Rules Violated | Evidence |
|---|---|---|---|---|
| 3sb-OrDO<br>POrGPOrGPOr<br>GPOGPOGDOGD<br>OGDOGPOGPOG<br>PO | 20 | 11 | (iii) | Minimal structure, no assembly (AUC/CD) |
| 3sb-OOrD<br>POGPOGPOGPOr<br>GPOrGPOrGPOG<br>POGDOGDOGDO | 25 | 11 | (iii) | no structure (CD) |
| 4sb-ctrl<br>POGDOGPOGDO<br>GDOGDOGPOGP<br>OGPKGPKGPKG<br>POGPKGPO | 38 | 14 | iii | no assembly, aggregation (AUC/CD/AFM/TEM) |
| 4sb-DOOr<br>POGDOGDOGDO<br>GDOGPOGPOGP<br>OGPOGPOrGP<br>OrGPOrGPOr<br>GPO | 39 | 14 | (iii) | Significant Structure loss, multiple species (CD) |
| 4sb-OOrD<br>POGPOGPOGPO<br>GPOrGPOrGP<br>OrGPOrGPOG<br>POGDOGDOGD<br>OGDO | 40 | 14 | (ii) | loss in stability, possible assembly (CD) |
| 4sbG-ctrl ("DOKctrl")<br>POGDOGPOGD<br>OGDOGDOGPO<br>GPOGPKGPKG<br>PKGPOGPKGP<br>OG | 13 | 14 | iii | no assembly, trimer (AUC/CD/TEM) |
| 4sbG-OOrD<br>POGPOGPOGPO<br>GPOrGPOrGP<br>OrGPOrGPOG<br>POGDOGDOGD<br>OGDOG | 41 | 14 | (iii) | loss in stability, fibers absent (CD/TEM) |
| 4sbG-OKD2ctrl<br>POGPOGPKGPK<br>GPKGPOGPKGP<br>OGPOGDOGPOG<br>DOGDOGDOG | 42 | 14 | iii | assembly/aggregation, no fibers (CD/TEM/DLS) |
| 4sbG-gap6<br>POGDOGPOGPK<br>GPKGPOGPOGP<br>KGPOGDKGDOG<br>POGPOGDOG | 43 | 14 | i | Stabilized by salt, assembly unlikely (CD/DLS) |

Example 3: Hydrogel Formation

The 42-residue peptide 4sbG-OKD2 ("OKD2"; $n_T$=3v−1=14, v=5; see Table 2) is another peptide that can be extracted from the 4sb-template (see FIG. 1f, and Example 1), similar to OKD, KDO and DOK. Like other 4sb-derived peptides, it assembles with a 14-residue "super-stagger" and forms extended triple helices. In terms of both morphology and thermostability, OKD2 nanofibers resemble those formed by OKD, its closest neighbor in sequence.

OKD2 assemblies form hydrogels at concentrations of 5 mg/mL or above. Peptide and buffer stocks in ultrapure water are mixed and diluted to obtain a 5 mg/mL OKD2 solution in 10 mM phosphate buffer, pH=7. This solution is placed in an airtight container, heated to 65° C. in a large water bath and annealed down to room temperature, overnight. The resulting hydrogel is subjected to rheological analysis (FIG. 15a).

Rheology on peptide hydrogels was performed on a TA ARES rheometer at the Soft Materials Laboratory at the University of Wisconsin—Madison, using 8-mm stainless-steel parallel-plate geometry with a 1 mm gap size. Strain sweeps (0.01-200%) maintained a fixed frequency of 2 rad/s, while a fixed strain of 1% was applied for frequency sweeps (0.1-100 rad/s). The results of such an experiment is on 5 mg/mL OKD2 is displayed in FIG. 15b.

The storage (G'=316 Pa) and loss moduli (G"=32 Pa) of the material is on par with previously characterized CMP hydrogels[19], and yields a high yield strain ($\gamma s$=185%). The observed order-of-magnitude difference between the loss and storage moduli is also a characteristic of hydrogels.

Experiments have confirmed that OKD, OKD2, OKDO and gap4 peptides from the 4sbG series form hydrogels. For these peptides at 1% concentration:

| 4sbG | G' | G" (units = kPa) |
|------|-----|------------------|
| OKD  | 0.5 | 0.05             |
| OKD2 | 1.5 | 0.05             |
| OKDO | 0.4 | (0)              |
| gap4 | 0.2 | (0.02)           |

The application includes the sequence listing that is concurrently filed in computer readable form. This sequence listing is incorporated by reference herein.

The invention is not limited to the embodiments set forth herein for illustration, but includes everything that is within the scope of the claims. Furthermore, all references cited herein are hereby incorporated by reference in their entirety and for all purposes as if fully set forth herein.

REFERENCES

1. Cohen, S. N., Chang, A. C. Y., Boyer, H. W., & Helling, R. B., Construction of biologically functional bacterial plasmids in-vitro. Proc. Natl. Acad. Sci. USA 70, 3240-3244 (1973).
2. Gibson, D. G. et al., Enzymatic assembly of DNA molecules up to several hundred kilobases. Nat. Methods 6, 343-345 (2009).
3. Khalil, A. S. & Collins, J. J., Synthetic biology: Applications come of age. Nat. Rev. Genet. 11, 367-379 (2010).
4. Seeman, N. C., Nanomaterials based on DNA. Annu. Rev. Biochem. 79, 65-87 (2010).
5. Zimenkov, Y. et al., Rational design of a reversible pH-responsive switch for peptide self-assembly. J. Am. Chem. Soc. 128, 6770-6771 (2006).
6. Banwell, E. F. et al., Rational design and application of responsive alpha-helical peptide hydrogels. Nat. Mat. 8, 596-600 (2009).
7. Brinckmann, J., Collagens at a glance. Top. Curr. Chem. 247, 1-6 (2005).
8. Meyers, M. A., Chen, P.-Y., Lin, A. Y.-M., & Seki, Y., Biological materials: Structure and mechanical properties. Prog. Mat. Sci. 53, 1-206 (2008).
9. Chattopadhyay, S. & Raines, R. T., Collagen-based biomaterials for wound healing. Biopolymers 101, 821-833 (2014).
10. Ricard-Blum, S., The collagen family. Cold Spring Harb. Perspect. Biol. 3, a004978 (2011).
11. Fields, G. B., Synthesis and biological applications of collagen-model triple-helical peptides. Org. Biomol. Chem. 8, 1237-1258 (2010).
12. Shoulders, M. D. & Raines, R. T., Collagen structure and stability. Annu. Rev. Biochem. 78, 929-958 (2009).
13. Siebler, C., Erdmann, R. S., & Wennemers, H., From azidoproline to functionalizable collagen. Chimia 67, 891-895 (2013).
14. Kotch, F. W. & Raines, R. T., Self-assembly of synthetic collagen triple helices. Proc. Natl. Acad. Sci. USA 103, 3028-3033 (2006).
15. Rele, S. et al., D-Periodic collagen-mimetic microfibers. J. Am. Chem. Soc. 129, 14780-14787 (2007).
16. Gottlieb, D., Morin, S. A., Jin, S., & Raines, R. T., Self-assembled collagen-like peptide fibers as templates for metallic nanowires. J. Mat. Chem. 18, 3865-3870 (2008).
17. Cejas, M. A. et al., Thrombogenic collagen-mimetic peptides: Self-assembly of triple helix-based fibrils driven by hydrophobic interactions. Proc. Natl. Acad. Sci. USA 105, 8513-8518 (2008).
18. Yamazaki, C. M. et al., A collagen-mimetic triple helical supramolecule that evokes integrin-dependent cell responses. Biomaterials 31, 1925-1934 (2010).
19. O'Leary, L. E. R., Fallas, J. A., Bakota, E. L., Kang, M. K., & Hartgerink, J. D., Multi-hierarchical self-assembly of a collagen mimetic peptide from triple helix to nanofibre and hydrogel. Nat. Chem. 3, 821-828 (2011).
20. Xu, F. et al., Compositional control of higher order assembly using synthetic collagen peptides. J. Am. Chem. Soc. 134, 47-50 (2012).
21. Sarkar, B., O'Leary, L. E. R., & Hartgerink, J. D., Self-assembly of fiber-forming collagen mimetic peptides controlled by triple-helical nucleation. J. Am. Chem. Soc. 136, 14417-14424 (2014).
22. Persikov, A. V., Ramshaw, J. A. M., Kirkpatrick, A., & Brodsky, B., Electrostatic interactions involving lysine make major contributions to collagen triple-helix stability. Biochemistry 44, 1414-1422 (2005).
23. Fallas, J. A., Gauba, V., & Hartgerink, J. D., Solution structure of an ABC collagen heterotrimer reveals a single-register helix stabilized by electrostatic interactions. J. Biol. Chem. 284, 26851-26859 (2009).
24. Coxeter, H. S. M., Crystal symmetry and its generalizations. Trans. Roy. Soc. Canada 51, 1-13 (1957).
25. Emmer, M. & Schattschneider, D. eds., M. C. Escher's Legacy: A Centennial Celebration. (Springer, New York, N. Y., 2003).
26. Tanrikulu, I. C. & Raines, R. T., Optimal interstrand bridges for collagen-like biomaterials. J. Am. Chem. Soc. 136, 13490-13493 (2014).
27. Gauba, V. & Hartgerink, J. D., Surprisingly high stability of collagen ABC heterotrimer: Evaluation of side chain charge pairs. J. Am. Chem. Soc. 129, 15034-15041 (2007).
28. Smulders, M. M. J. et al., How to distinguish isodesmic from cooperative supramolecular polymerisation. Chem.—Eur. J. 16, 362-367 (2010).
29. Persikov, A. V., Ramshaw, J. A. M., & Brodsky, B., Prediction of collagen stability from amino acid sequence. J. Biol. Chem. 280, 19343-19349 (2005).
30. Gelman, R. A., Williams, B. R., & Piez, K. A., Collagen fibril formation: Evidence for a multistep process. J. Biol. Chem. 254, 180-186 (1979).

31. Bai, H. Y., Xu, K., Xu, Y. J., & Matsui, H., Fabrication of Au nanowires of uniform length and diameter using a monodisperse and rigid biomolecular template: Collagen-like triple helix. Angew. Chem. Int. Ed. 46, 3319-3322 (2007).
32. Persikov, A. V., Ramshaw, J. A., Kirkpatrick, A., & Brodsky, B., Amino acid propensities for the collagen triple-helix. Biochemistry 39, 14960-14967 (2000).
33. Chen, Y.-S., Chen, C.-C., & Horng, J.-C., Thermodynamic and kinetic consequences of substituting glycine at different positions in a Pro-Hyp-Gly repeat collagen model peptide. Biopolymers 96, 60-68 (2011).
34. Jiang, T., Xu, C., Zuo, X., & Conticello, V. P., Structurally homogeneous nanosheets from self-assembly of a collagen-mimetic peptide. Angew. Chem. Int. Ed. 53, 8367-8371 (2014).
35. McGuinness, K., Khan, I. J., & Nanda, V., Morphological diversity and polymorphism of self-assembling collagen peptides controlled by length of hydrophobic domains. ACS Nano 8, 12514-12523 (2014).
36. Wess, T. J., Collagen fibril form and function. Adv. Protein Chem. 70, 341-374 (2005).
37. Kaur, P. et al., Three-dimensional directed self-assembly of peptide nanowires into micrometer-sized crystalline cubes with nanoparticle joints. Angew. Chem. Int. Ed. 49, 8375-8378 (2010).

We claim:

1. A synthetic symmetrical triple helical collagen assembly comprising:
   a plurality of self-assembling collagen mimetic peptides comprising Xaa-Yaa-Gly tripeptide repeats, wherein the number of tripeptide repeats ($n_T$) is $3v\pm1$, wherein v is a positive integer, wherein the peptide is n residues in length, wherein $n=n_T \times 3$;
   wherein the collagen mimetic peptides self-assemble with an $n_t$-residue offset to form the symmetrical triple helical collagen assembly.

2. The synthetic symmetrical triple helical collagen assembly of claim 1, wherein the collagen mimetic peptides comprise the tripeptides in the following sequence:
   $(POG)_n(PKG/DOG)_m(POG/DKG)_p (DOG/PKG)_q(POG)_r$
   wherein n, m, p, q, and r are selected from 0 or a positive integer of 1-10, and wherein $n_T=n+m+p+q+r=3v\pm1>0$.

3. The synthetic symmetrical triple helical collagen assembly of claim 1, wherein neighboring self-assembling collagen mimetic peptides of the triple helical collagen assembly are offset by Xaa-Yaa-Gly tripeptide repeats.

4. The synthetic symmetrical triple helical collagen assembly of claim 1, wherein the Yaa amino acid of a $K_t$ Xaa-Yaa-Gly tripeptide repeat comprises an amino acid capable of charge pairing and the Xaa amino acid of a $D_t$ Xaa-Yaa-Gly tripeptide repeat comprises an amino acid capable of charge pairing with the Yaa amino acid of the $K_t$ Xaa-Yaa-Gly tripeptide repeat on a neighboring self-assembling collagen mimetic peptide of the triple helical collagen assembly, and wherein $K_t$ is a positive integer from 1 to nT and $D_t=(K_t\pm v+1)$ mod nT.

5. The synthetic symmetrical triple helical collagen assembly of claim 1, comprising a charged block at an end of the triple helical collagen assembly.

6. The synthetic symmetrical triple helical collagen assembly of claim 5, wherein the triple helical collagen assembly is stabilized by an interstrand interaction between the Yaa amino acid of the $K_t$ Xaa-Yaa-Gly tripeptide repeat and the Xaa amino acid of a $D_t$ Xaa-Yaa-Gly tripeptide repeat on the neighboring self-assembling collagen mimetic peptide of the triple helical collagen assembly.

7. The synthetic symmetrical triple helical collagen assembly of claim 6, wherein the interstrand interaction comprises at least one interstrand salt bridge.

8. The synthetic symmetrical triple helical collagen assembly of claim 7, wherein the at least one interstrand salt bridge is formed from a lysine residue in the Yaa position of the $K_t$ Xaa-Yaa-Gly tripeptide repeat and an aspartic acid residue in the Xaa position of the $D_t$ Xaa-Yaa-Gly tripeptide repeat on the neighboring self-assembling collagen mimetic peptide.

9. The synthetic symmetrical triple helical collagen assembly of claim 7, wherein the at least one interstrand salt bridge comprises a first interstrand salt bridge and a second interstrand salt bridge, wherein the first interstrand salt bridge is formed from a lysine residue in the Yaa position of the $K_t$ Xaa-Yaa-Gly tripeptide repeat on a first strand and an aspartic acid residue in the Xaa position of the $D_t$ Xaa-Yaa-Gly tripeptide repeat on the neighboring self-assembling collagen mimetic peptide on a second strand and the second interstrand salt bridge is formed from a lysine residue in the Yaa position of the $K_t$ Xaa-Yaa-Gly tripeptide repeat on a second strand and an aspartic acid residue in the Xaa position of the $D_t$ Xaa-Yaa-Gly tripeptide repeat on the neighboring self-assembling collagen mimetic peptide on a third strand.

10. The synthetic symmetrical triple helical collagen assembly of claim 7, wherein the at least one interstrand salt bridge is formed from a lysine residue in the Yaa position on a first strand and an aspartic acid residue in the Xaa position on a second strand at a three residue offset.

11. The synthetic symmetrical triple helical collagen assembly of claim 8, wherein greater than about 90% of the available lysine residues and available aspartic acid residues are linked by an interstrand salt bridge.

12. The synthetic symmetrical triple helical collagen assembly of claim 1, wherein nT is $3v+1$.

13. The synthetic symmetrical triple helical collagen assembly of claim 1, wherein nT is $3v-1$.

14. The synthetic symmetrical triple helical collagen assembly of claim 1, wherein v is 5.

15. The synthetic symmetrical triple helical collagen assembly of claim 14, wherein the triple helical collagen assembly comprises a homotrimer wherein the homotrimer comprises about 4 salt bridges per about 14 residues.

16. The synthetic symmetrical triple helical collagen assembly of claim 1, wherein the Xaa-Yaa-Gly tripeptide repeats comprises Xaa-Yaa-Gly tripeptide repeats of ProLysGly, AspHypGly, ProHypGly or combinations thereof.

17. The synthetic symmetrical triple helical collagen assembly of claim 1, wherein the Xaa-Yaa-Gly tripeptide repeats are selected from the group consisting of POG, PKG, DOG, DKG and combinations thereof.

18. The synthetic symmetrical triple helical collagen assembly of claim 1, wherein the each strand of the helix is at least about 500 residues.

19. The synthetic symmetrical triple helical collagen assembly of claim 1, wherein the assembly is about 200 nm in length.

20. The synthetic symmetrical triple helical collagen assembly of claim 1, wherein the assembly comprises a central Xaa-Yaa-Gly tripeptide repeat and Xaa of the central Xaa-Yaa-Gly tripeptide repeat is proline or aspartic acid and Yaa of the central Xaa-Yaa-Gly tripeptide repeat is lysine to reduce blunt end association.

21. The synthetic symmetrical triple helical collagen assembly of claim 1, wherein the self-assembling collagen mimetic peptide comprises a terminal Xaa-Yaa-Gly tripeptide repeat and Yaa of the terminal Xaa-Yaa-Gly tripeptide repeat is hydroxyproline to reduce blunt end association.

22. The synthetic symmetrical triple helical collagen assembly of claim 1, wherein the symmetrical triple helical collagen assembly has a melting temperature (Tm) of greater than about 37° C.

23. The synthetic symmetrical triple helical collagen assembly of claim 1, wherein the symmetrical triple helical collagen assembly has a melting temperature (Tm) of greater than about 45° C.

24. The synthetic symmetrical triple helical collagen assembly of claim 1, wherein the Xaa-Yaa-Gly tripeptide repeats comprises any one of sequence SEQ ID NO: 2-9, 10, 12, 14-18, 22, or 27-37.

25. The synthetic symmetrical triple helical collagen assembly of claim 1, wherein the collagen mimetic peptides comprise the tripeptides in the following sequence:

(POG)n(PKG/DOG)m(POG/DKG)p (DOG/PKG)q (POG)r wherein n, m, p, q, and r are selected from 0 or a positive integer of 1-10, and wherein nT=n+m+p+q+r=3v±1>0.

* * * * *

UNITED STATES PATENT AND TRADEMARK OFFICE
CERTIFICATE OF CORRECTION

PATENT NO. : 12,162,924 B2
APPLICATION NO. : 17/554650
DATED : December 10, 2024
INVENTOR(S) : Ronald T. Raines et al.

It is certified that error appears in the above-identified patent and that said Letters Patent is hereby corrected as shown below:

In the Specification

Column 2, Line 56, "(PKD/DOC)$_m$" should be --(PKD/DOG)$_m$--.

Column 7, Line 40, "(Hyp, 0)" should be --(Hyp, O)--.

Column 12, Line 42, "(Lys), 0 is" should be --(Lys), O is--.

Column 13, Line 12, "n+m=n+m+p+q+r=3v ±1>0" should be --$n_T$=n+m+p+q+r=3v ±1>0--.

Column 16, Line 31, "NC atom" should be --$N^\epsilon$ atom--.

Column 18, Line 50, "(FIG. 10." should be --(FIG. 1f)--.

Column 27, Line 1, "o." should be --Ø.--.

Column 27, Line 22, "$n_T$ 3v" should be --$n_T \neq 3v$--.

Signed and Sealed this
Thirteenth Day of May, 2025

Coke Morgan Stewart
*Acting Director of the United States Patent and Trademark Office*